(12) United States Patent
Duff et al.

(10) Patent No.: US 7,161,060 B1
(45) Date of Patent: Jan. 9, 2007

(54) TRANSGENIC MICE COMPRISING A GENOMIC HUMAN TAU TRANSGENE

(75) Inventors: Karen Duff, New York, NY (US); Peter Davies, Rye, NY (US)

(73) Assignees: Albert Einstein College of Medicine of Yeshiva University, Bronx, NY (US); Research Foundation for Mental Hygiene, Inc., Menands, NY (US)

( * ) Notice: Subject to any disclaimer, the term of this patent is extended or adjusted under 35 U.S.C. 154(b) by 522 days.

(21) Appl. No.: 10/620,840

(22) Filed: Jul. 16, 2003

Related U.S. Application Data

(60) Provisional application No. 60/396,699, filed on Jul. 16, 2002, provisional application No. 60/405,363, filed on Aug. 21, 2002.

(51) Int. Cl.
*A01K 67/027* (2006.01)
*A01K 67/00* (2006.01)
*C12N 15/00* (2006.01)
*C12N 15/63* (2006.01)
*C07H 21/04* (2006.01)

(52) U.S. Cl. ............ 800/18; 800/13; 800/21; 536/23.5; 536/24.1; 435/455

(58) Field of Classification Search ............ 800/13, 800/18, 21; 536/23.5, 24.1; 435/455
See application file for complete search history.

(56) References Cited

U.S. PATENT DOCUMENTS 6,593,512 B1 7/2003 Vitek et al.

FOREIGN PATENT DOCUMENTS

WO WO-0153340 A2 7/2001

OTHER PUBLICATIONS

Kappel et al., 1992, Current Opinion in Biotechnology, vol. 3, p. 548-553, IDS.*
Sigmund, C., Jun. 2000, Arterioscler. Thromb. Vasc. Biol., p. 1425-1429, IDS.*
Houdebine, L-M., 2002, Journal of Biotechnology, vol. 98, p. 145-160, IDS.*
Lee et al., 1999, Neuron, vol. 24, No. 3, p. 507-510, IDS.*
Duff et al., 2000, Neurobiology of diseases, vol. 7, p. 87-98.*
Refolo et al., Oct. 1999, Society for Neuroscience Abstracts, vol. 25, No. 1-2, pp. 790, IDS.*
Andreadis, A., et al., "Structure and Novel Exons of the Human tau Gene", *Biochemistry*, 31, (1992), 10626-10633.
Aranda-Abreu, G E., et al., "Embryonic lethal abnormal vision-like RNA-binding proteins regulate neurite outgrowth and tau expression in PC12 cells.", *Journal of Neuroscience*, 19(16), (1999), 6907-17.
Behar, L., et al., "cis-acting signals and trans-acting proteins are involved in tau mRNA targeting into neurites of differentiating neuronal cells.", *International Journal of Developmental Neuroscience*. 13(2), (1995), 113-27.
Braak, E, et al., "A sequence of cytoskeleton changes related to the formation of neurofibrillary tangles and neuropil threads", *Acta Neuropathologica*. 87(6), (1994), 554-67.
Brion, J P., et al., "Transgenic expression of the shortest human tau affects its compartmentalization and its phosphorylation as in the pretangle stage of Alzheimer's disease.", *American Journal of Pathology*. 154(1), (1999), 255-70.
Dawson, Hana N., et al., "Inhibition of Neuronal Maturation in Primary Hippocampal Neurons from Tau Deficient Mice", *Cell Science*, 114, (2001), 1179-1187.
Dawson, Hana N., et al., "Tau Distribution in a Human Tau Gene Transgenic/Mouse Tau Knock-Out Model", *Society for Neuroscience*, 25, Miami Beach, FL, Abstract No. 317.1,(1999), 1 pg.
Goedert, M., et al., "Cloning and Sequencing of the cDNA Encoding a Core Protein of the Paired Helical Filament of Alzheimer Disease: Identification as the Microtubule-Associated Protein Tau", *Proc. Natl. Acad. Sci. USA*, 85, (Jun. 1988), 4051-4055.
Goedert, M., et al., "Cloning and Sequencing of the cDNA encoding an isoform of microtubule-associated Protein Tau Containing Four Tandem Repeats: differential expression of tau protein mRNAs in human brain", *The EMBO Journal*, 8, (1989), 393-399.
Goedert, M, et al., "Tau gene mutation in familial progressive subcortical gliosis", *Nature Medicine*. 5(4), (1999), 454-7.
Gotz, J., et al., "Somatodendritic Localization and Hyperphosphorylation of Tau Protein in Transgenic Mice Expressing the Longest Human Brain Tau Isoform", *The EMBO Journal*, 14, (1995), 1304-1313.
Grover, A, et al., "5' splice site mutations in tau associated with the inherited dementia FTDP-17 affect a stem-loop structure that regulates alternative splicing of exon 10", *Journal of Biological Chemistry*. 274(21), (1999), 15134-43.

(Continued)

*Primary Examiner*—Shin-Lin Chen
(74) *Attorney, Agent, or Firm*—Schwegman, Lundberg, Woessner & Kluth, P.A.

(57) ABSTRACT

The invention provides transgenic mice comprising tau transgenes, and methods of preparing and using the transgenic mice. For example, the invention provides a transgenic mouse, the genome of the cells of which stably comprise a DNA molecule which comprises a human genomic DNA sequence comprising a human tau promoter and which DNA sequence encodes human tau.

6 Claims, 15 Drawing Sheets

OTHER PUBLICATIONS

Haudebine, L., "The Methods to Generate Transgenic Animals and to Control Transgene Expression", *Journal of Biotechnology*, 98, (2002), 145-160.

Ikonomovic, M D., et al., "The loss of GluR2(3) immunoreactivity precedes neurofibrillary tangle formation in the entorhinal cortex and hippocampus of Alzheimer brains", *Journal of Neuropathology & Experimental Neurology*, 56(9), (1997), 1018-27.

Jicha, G A., et al., "A conformation- and phosphorylation-dependent antibody recognizing the paired helical filaments of Alzheimer's disease", *Journal of Neurochemistry*. 69(5), (1997), 2087-95.

Jicha, G A., et al., "Alz-50 and MC-1, a new monoclonal antibody raised to paired helical filaments, recognize conformational epitopes on recombinant tau", *Journal of Neuroscience Research*. 48(2), (1997), 128-32.

Jicha, G A., et al., "Sequence requirements for formation of conformational variants of tau similar to those found in Alzheimer's disease", *Journal of Neuroscience Research*, 55(6), (1999), 713-23.

Kappel, C. A., et al., "Regulating Gene Expression in Transgenic Animals", *Current Opinion in Biotechnology*, 3, (1992), 548-553.

Kosik, K S., et al., "Tau in situ hybridization in normal and Alzheimer brain: localization in the somatodendritic compartment", *Annals of Neurology*. 26(3), (1989), 352-61.

Lee, V. M., et al., "Neurodegenerative Tauopathies: Human Disease and Transgenic Mouse Models", *Neuron*, 24(3), (Nov. 1999), 507-510.

Murrell, J. R., et al., "Familial Multiple-System Tauopathy with Presenile Dementia Is Localized to Chromosome 17", *Am. J. Hum. Genet.*, 61, (1997), 1131-1138.

Refolo, L., et al., "Phenotype of Transgenic Mice Over-Expressing A Normal Human Tau Gene", *Society for Neuroscience Abstracts*, 25 (1-2), (Oct. 1999), 790.

Sigmund, C. D., "Viewpoint: Are Studies in Genetically Altered Mice Out of Control?", *Arterioscler Thromb Vasc Biol*, (Jun. 2000), 1425-1429.

\* cited by examiner

A) RT-PCR Exon 1-5

B) RT-PCR Exon 9-11

SEQUENCE LISTING

<160> NUMBER OF SEQ ID NOS: 9

<210> SEQ ID NO 1
<211> LENGTH: 20
<212> TYPE: DNA
<213> ORGANISM: Mus musculus

<400> SEQUENCE: 1
caccaaaatc cggagaacga                                               20

<210> SEQ ID NO 2
<211> LENGTH: 20
<212> TYPE: DNA
<213> ORGANISM: Mus musculus

<400> SEQUENCE: 2
ctttgctcag gtccaccggc                                               20

<210> SEQ ID NO 3
<211> LENGTH: 20
<212> TYPE: DNA
<213> ORGANISM: Homo sapiens

<400> SEQUENCE: 3
ctccaaaatc agggggatcgc                                              20

<210> SEQ ID NO 4
<211> LENGTH: 20
<212> TYPE: DNA
<213> ORGANISM: Homo sapiens

<400> SEQUENCE: 4
ccttgctcag gtcaactggt                                               20

<210> SEQ ID NO 5

<400> SEQUENCE: 5

000

<210> SEQ ID NO 6
<211> LENGTH: 19
<212> TYPE: DNA
<213> ORGANISM: Mus musculus

<400> SEQUENCE: 6
tccgctgtcc tcttctgtc                                                19

<210> SEQ ID NO 7
<211> LENGTH: 19
<212> TYPE: DNA
<213> ORGANISM: Mus musculus

<400> SEQUENCE: 7
ttctcgtcat ttcctgtcc                                                19

<210> SEQ ID NO 8
<211> LENGTH: 19
<212> TYPE: DNA
<213> ORGANISM: Homo sapiens

<400> SEQUENCE: 8

```
tgaaccagga tggctgagc                                                  19
```

<210> SEQ ID NO 9
<211> LENGTH: 21
<212> TYPE: DNA
<213> ORGANISM: Homo sapiens

<400> SEQUENCE: 9

```
ttgtcatcgc ttccagtccr t                                               21
```

TRANSGENIC MICE COMPRISING A GENOMIC HUMAN TAU TRANSGENE

RELATED APPLICATION(S)

This application claims benefit under 35 U.S.C. § 119 (e) of U.S. Provisional Application No. 60/396,699 filed Jul. 16, 2002 and U.S. Provisional Application No. 60/405,363 filed Aug. 21, 2002, which are incorporated herein by reference.

STATEMENT OF GOVERNMENT RIGHTS

The invention was made, at least in part, with a grant from the Government of the United States of America (grants AG146133, AG17216, NS37132-01 and NIMH28623 from the National Institutes of Health). The Government may have certain rights to the invention.

BACKGROUND OF THE INVENTION

The human tau protein has been implicated in the pathogenesis of several human neurodegenerative diseases including Alzheimer's disease (AD) and frontal temporal lobe dementia (Hardy et al. 1998, Spillantini and Godert 1998). The pathology of AD is defined as the presence of amyloid-containing plaques and neurofibrillary tangles (NFTs) composed of tau arranged into paired helical filaments (PHFs). Mutations in the tau gene lead to a range of tauopathies (termed Fronto-Temporal Dementia and Parkinsonism linked to chromosome 17 (FTDP-17) where tau takes the form of PHF (Spillantini et al. 1996, Poorkaj et al. 1998, Hutton et al. 1998) or twisted ribbons (Spillantini et al. 1997, 1998, Hutton et al. 1998, Reed et al. 1998). Although the mechanisms underlying the development of tauopathy in these diseases are unknown, hyperphosphorylation of tau has been linked to AD (Iqbal and Iqbal 1996), and disruption of microtubule binding and assembly has been linked to FTDP-17 missense mutations (Hasegawa et al. 1998, Hong et al. 1998).

Human tau is alternatively spliced to generate six isoforms that differ in the presence of absence of exons 2, 3 or 10 (Godert et al. 1989, Andreadis et al. 1992). Splicing out of exon 10 generates a tau protein with 3 microtubule binding domain repeats (3R), whereas its inclusion generates tau with 4 repeats (4R). The normal human brain maintains an approximately equal ratio of 4R to 3R tau but this ratio is shifted in favor of more 4R tau in FTDP-17 patients with splice site mutations (Godert and Jakes 1990, Spillantini et al. 1998, Hong et al. 1998, Godert et al. 1999, Grover et al. 1999). Biochemical evidence suggests that microtubule binding and assembly is disrupted by some missense mutations in tau (Hasegawa et al. 1998, Hong et al. 1998, Dayanandan et al. 1999), however, the mechanism by which excess 4R tau causes neuronal degeneration is less clear. Given that excess 4R tau is detrimental to humans, it is surprising that the normal adult mouse makes 4R tau exclusively (Gotz et al. 1995, Kampers et al. 1999), although it is possible that in FTDP-17, a shift in the normal ratio of tau isoforms is pathogenic rather than their absolute levels.

Thus, what is needed is a non-human animal model which expresses human tau, e.g., to examine the normal biology of tau and to provide a model for tauopathies where the ratio of tau isoforms are shifted.

SUMMARY OF THE INVENTION

The invention provides a transgenic rodent, e.g., a rat or a mouse, the genome of the cells of which are augmented with a human genomic DNA sequence encoding tau. Preferably, the expression of the human genomic DNA sequence results in the presence of at least one, and preferably two or more, e.g., all six, isoforms of human tau. It is envisioned that the human genomic DNA sequence comprises wild-type human tau sequences, as well as sequences which have alterations, e.g., deletions, insertions or mutations, for example, a splice site or missense mutation, e.g., one encoding an amino acid substitution, such as those which result in a shift in the ratio of the isoforms. Preferably, the alterations yield tau protein that is associated with dementing disorders, including neurodegenerative disorders, in humans. As described hereinbelow, to examine the normal cellular function of tau and its role in pathogenesis, transgenic mice were prepared that over-express a tau transgene derived from a human PAC that contains the coding sequence, intronic regions and regulatory regions of the human gene. All six isoforms of human tau are represented in the transgenic mouse brain at the mRNA and protein level and the human tau is distributed in neurites and at synapses, but is absent from cell bodies. A comparison between the genomic tau mice and transgenic mice that over-express a tau cDNA transgene shows that overall, the distribution of tau is similar in the two lines, but human tau is located in the somato-dendritic compartment of many neurons in the cDNA mice. Tau-immunoreactive axonal swellings were found in the spinal cords of the tau cDNA mice, which correlated with a hind-limb abnormality whereas neuropathology was essentially normal in the tau genomic DNA mice up to eight months of age. Further provided are progeny of human genomic tau mice, e.g., progeny of a cross between genomic tau mice and tau knock out mice, e.g., a C129/C57B16 knock out. As described hereinbelow, such progeny mice had somatodendritic localization of tau which was in an abnormal conformation. Thus, in one embodiment of the invention, the human genomic tau DNA mice do not express murine tau, e.g., due to a knock out of the endogenous murine tau gene(s). Onset of abnormal pathologies in tau transgenic mice can occur at any time in development. For example, in one embodiment of the invention, the human genomic tau mice present a normal phenotype early in life; however, during the course of development, the human tau genomic mice develop one or more abnormal pathologies, e.g., motor and/or neurological pathologies. In another embodiment, abnormal pathologies may be present before or immediately after birth and optionally those pathologies progressively worsen.

The invention also provides a method of preparing a transgenic rodent of the invention. The method comprises contacting a rodent cell which can give rise to an organism, e.g., a totipotent cell such as a fertilized embryo, with an isolated and purified DNA molecule comprising a human genomic DNA sequence encoding tau so as to yield a transformed cell. The transformed cell is manipulated so as to yield a rodent. Then it is determined whether the rodent comprises cells comprising the human genomic DNA sequence encoding tau, i.e., it is a transgenic rodent. Preferably, the rodent expresses human tau. For example, the rodent may express all six forms of human tau, a subset of the human isoforms, and/or an altered ratio of the human isoforms. The expression of a subset of isoforms, e.g., one or more but less than all six of the human isoforms, or an altered ratio of human isoforms, may be the result of one or more alterations in the human genomic DNA sequence relative to a sequence, the expression of which results in the presence of all six human isoforms in the rodent.

Further provided is an isolated and purified DNA molecule comprising a human genomic DNA sequence encoding tau.

Also provided is a method to employ the rodent of the invention, e.g., to screen for an agent that inhibits or reduces neurodegeneration or tauopathies, e.g., such as those which are associated with Alzheimer's disease, frontal temporal lobe dementia, FTPD-17, and the like.

The invention also provides a transgenic rodent comprising a humanized tau gene. For example, an isolated and purified murine DNA sequence encoding tau is altered so that at least one, preferably at least one fourth, and more preferably at least a majority, of the codons in the murine tau coding region are humanized, thus, providing a humanized murine tau DNA sequence. The humanized murine tau DNA sequence may encode native murine tau or may comprise alterations, i.e., insertions, deletions, or mutations, e.g, which result in amino acid substitutions, or any combination thereof. Then the isolated and purified humanized murine tau DNA sequence is introduced into a murine cell that can give rise to an organism, e.g., a totipotent cell such as a fertilized embryo, so as to yield a transformed murine cell. The transformed cell is manipulated so as to yield a mouse. Then it is determined whether the mouse comprises cells comprising the humanized murine tau DNA sequence, i.e., it is a transgenic mouse. Preferably, the transgenic mouse of this embodiment of the invention expresses the humanized tau. More preferably, the expression of the humanized tau in the transgenic mouse is associated with the development of a pathology in the mouse.

BRIEF DESCRIPTION OF THE DRAWINGS

FIGS. 15A–C. Neurons prepared from non-transgenic mice (A) failed to show staining with MC1, an antibody that recognizes tau in an abnormal conformation, at any age studied (up to 24 wiv). Slices from 8c mice developed immunoreactive tangles only in the oldest cultures (24 wiv) (data not shown). Slices from P301L and hTau mice however, developed MC1 immunoreactive tangles at the earliest stage examined (2 wiv). Sections from a 6 week old P301L (B) or hTau (C) mouse brain show MC1 immunolabeling in cell bodies and processes in cortical areas (magx100).

DETAILED DESCRIPTION OF THE INVENTION

Figure 1:
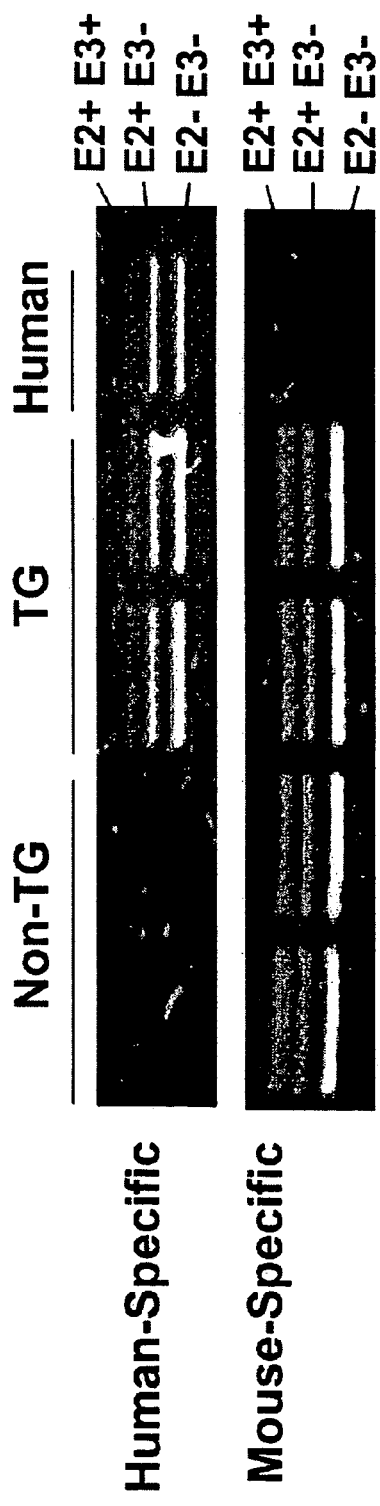
FIG. 1 is an RT-PCR analysis of splice isoforms in genomic 8c mice compared to human brain. RT-PCR was performed using primers that spanned the alternatively spliced exons 2, 3, and 10 (A and B, respectively). Primers were designed to be specific for human or mouse tau and exon fragments were identified based on their size.
Figure 1:
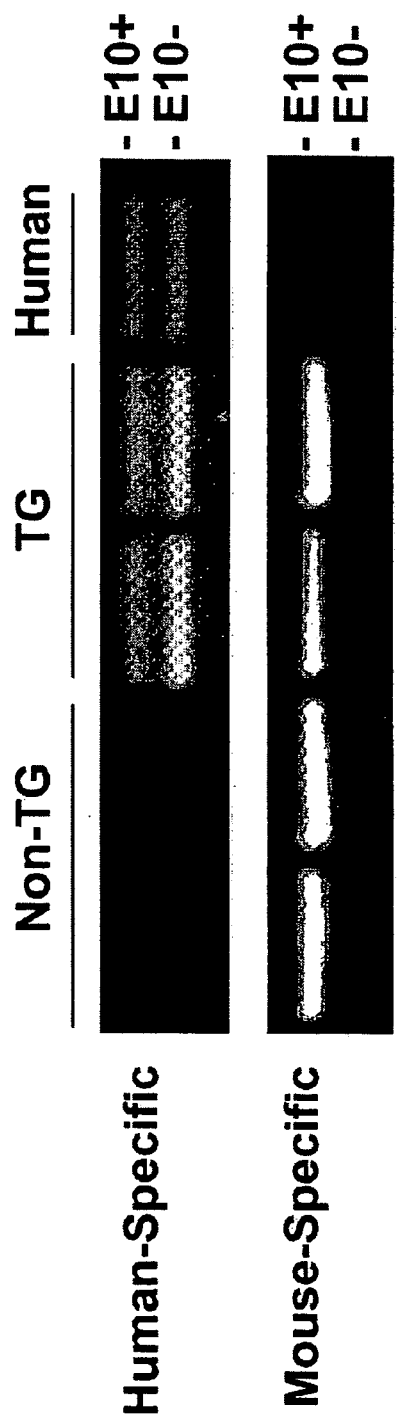

The invention provides a transgenic rodent comprising a tau transgene, e.g., a humanized rodent tau transgene or a human genomic tau transgene, and methods of preparing and using the transgenic rodents. The transgenic rodents are prepared with an isolated and purified DNA sequence encoding tau. The isolated and purified DNA sequence which encodes tau may represent native sequences, including tau sequences that are not associated with any pathology in humans and tau sequences that are associated with pathology in humans, or may represent novel sequences, e.g., humanized murine tau sequences. The expression of the DNA sequence in the transgenic rodent results in tau protein. The transgenic rodents of the invention are useful to test agents, e.g., agents that inhibit or prevent pathological neurodegeneration, to determine which environmental or genetic factors other than tau predispose an organism to a dementing disorder, or as a source of tau, e.g., to prepare antibodies.

The invention will be further described by the following non-limiting examples.

EXAMPLE I

Preparation of Human Genomic Tau Transgenic Mice Methods

Transgene preparation. To isolate the human tau gene, three human genomic libraries were screened either by PCR using primers to exon 1 or 9 of the human tau gene, or by hybridization with restriction fragments derived from the human cDNA clone, p19 (kind gift of G. Lee). The libraries had been generated in either a PAC vector (Genome Systems) or a BAC vector (Genome Systems and Research Genetics). A total of eight positive clones were identified. Positive clones and human genomic DNA were subjected to standard PCR to test for the presence of each exon, and to long range PCR using the High Fidelity Expand Kit (Boehringer Mannheim) and primers spanning introns of the human tau gene. DNA from clones and human genomic DNA was digested with a range of enzymes and the fragments were separated by Pulsed Field Gel Electrophoresis (PFGE) or conventional electrophoresis. Resolved DNA was transferred to nylon membrane and hybridized with tau specific PCR derived probes. Comparison to human DNA showed that two PACs [GS 61d06 (#30) and 24i13 (#32)] and one BAC [RG 369n16] were essentially intact for the coding portions of the tau gene. The BAC clone, however, lacked the non-coding exon, exon 14, and was excluded.

Linear, exogenous DNA integrates into the mouse genome far more efficiently than circular DNA. An attempt was made to linearize the transgene, or remove it from the vector backbone, by restriction enzyme digestion. A total of fifteen enzymes were analyzed (ApaLI, AscII, AvrII, BsaBI, BspHI, BssSI, DraIII, DrdI, NsiI, PacI, PmeI, PspAI, Psp1406, SgrAI, Sse8387) but all cut the DNA at multiple sites. Only SrfI appeared to cut once within the vector and within the gene, but the latter site was within the coding region.

Generation of transgenic mice. Intact, circular PAC DNA from clone 32 was purified using KB-100 Magnum columns (Genome Systems). DNA was eluted and diluted in microinjection buffer containing 10 mM Tris pH 7.4, 0.1 mM EDTA, pH 8, 100 mM NaCl, 300 μM spermine and 70 μM spermidine in pyrogen-free distilled water (Gibco-BRL). DNA at 3–5 ng/μl was injected into fertilized embryos from a cross between Swiss Webster female donors and B6D2F1 males (Taconic farms). Tail DNA from founder pups was digested with restriction enzymes and hybridized with exon specific probes, using similarly digested human DNA as a control to test for transgene integrity. Positive founder pups were expanded onto a Swiss Webster/B6D2F1 hybrid background.

RT PCR analysis of splice isoforms in genomic-tau mice and human brain. RNA was isolated from human cortex and hemi-brains of transgenic and non-transgenic animals (line 8c) using the Trizol reagent (Life Technologies). To examine the alternate splicing of the microtubule binding domain repeat region encoded by exon 10, primers were designed that specifically recognized mouse or human exons 9 and 11. Primer sequences used were as follows: Mouse exon 9F 5'-CACCAAAATCCGGAGAACGA (SEQ ID NO:1), Mouse exon 11R 5'CTTTGCTCAGGTCCACCGGC (SEQ ID NO:2), Human exon 9F 5' CTCCAAAATCAGGGGATCGC (SEQ ID NO:3), Human exon 11R 5'-CCTTGCTCAGGTCAACTGGT (SEQ ID NO:4). Splicing around the N terminal insert domain encoded by exons 2 and 3 was assessed using primers that recognized exons 1 and 5. Primer sequences used were as follows: Mouse exon 1F 5'

TCCGCTGTCCTCTTCTGTC (SEQ ID NO:6), Mouse exon 5R 5' TTCTCGTCATTTCCTGTCC (SEQ ID NO:7), Human exon 1F 5'-TGAACCAGGATGGCTGAGC (SEQ ID NO:8), Human exon 5R 5', TTGTCATCGCTTC-CAGTCCRT (SEQ ID NO:9). PCR conditions were 30 cycles of 94° C. for 30 seconds, 62° C. for 30 seconds and 72° C. for 45 seconds with a final 72° C. extension phase for 10 minutes. Mouse and human-specific RT-PCR products were analyzed by gel electrophoresis. Products corresponding to exon 10+ tau mRNA gave a band at 390 bp while products corresponding to exon 10– mRNA gave a band at 297 bp. RT-PCR products corresponding to tau mRNA with exons 2 and 3 (2+3+) gave a band at 428 bp, 2+3– mRNA products were 341 bp whereas 2–3– mRNA products were 253 bp.

ELISA assay. Mouse hemi-brains and human cortex samples were Dounce homogenized, at a w/v ratio of 100 mg/ml, in TBS containing protease and phosphatase inhibitors. The homogenates were centrifuged at 15,000×g for 20 minutes and the supernatants recovered, aliquoted and stored frozen at −80° C. Supernatants were serially diluted and used to coat Maxi-sorb ELISA plates. Samples were evaporated to dryness and the plates were blocked in TBS containing 5% non-fat, dry milk for 1 hour at room temperature. Anti-tau monoclonals (TG5 for total tau and CP27 for human tau) were added at 1:20 dilutions, and were incubated overnight at 4° C. Plates were washed in TBS containing 0.5% Tween 20. Bound anti-tau antibodies were detected using goat anti-mouse secondary antibodies coupled to HRP. Plates were washed and bound antibodies were quantified using ABTS peroxidase substrate (Biorad).

Immunoblot analysis of heat stable and dephosphorylated tau. Mouse hemi-brains and human cortex samples were Dounce homogenized on ice, at a w/v ratio of 100 mg tissue/ml, in 50 mM Tris, pH 7.5, 0.8 M NaCl, 5% β-mercaptoethanol. The homogenate was centrifuged at 15,000×g for 20 minutes. To prepare heat stable tau, the supernatant was heated at 95° C. for 10 minutes and cooled to room temperature. The heat stable tau prep was then heated at 95° C. for 10 minutes and cooled to room temperature. The heat stable tau prep was then dialyzed against 50 mM Tris pH 7.5, 1 mM EDTA, 0.1 mM PMSF. Tau was dephosphorylated by incubating the dialyzed heat stable fraction for 1 hour at 37° C. with 13 U/ml of *E. coli* alkaline phosphatase (according to a method described in Goedert et al., 1994). Samples were separated on a 10% Tris-Tricine gel, then electrophoretically transferred to PVDF membrane blocked in PBS containing 5% non-fat, dry milk. Membranes were probed with the following anti-tau monoclonal antibodies: TG5, CP27, CP13 (phosphoserine 202) and PHF-1 (phosphoserine 396 and 404). Bound anti-tau antibodies were detected using HRP coupled anti-mouse secondary antibodies (Southern Biochemicals) and were visualized by enhanced chemiluminescence (Pierce).

Immunoblot analysis of phospho-epitopes. Mouse hemi-brains were Dounce homogenized in TBS (50 mM Tris, pH 7.5, 150 mM NaCl) containing protease inhibitors (Complete, Boehringer Mannheim) and phosphatase inhibitors (1 mM sodium orthovanadate and 20 mM sodium fluoride) at a w/v ratio of 100 mg/ml. Human brain tissue was homogenized in the same buffer at the same w/v ratio. The homogenate was centrifuged at 75,000×g for 1 hour, at 4° C. Soluble tau was assessed in the supernatant. Cytoskeleton-associated tau was assessed in the pelleted fraction resuspended in TBS with 2% SDS. Samples were analyzed by immunoblotting.

Immunohistochemistry. Mice were anesthetized with Nembutal and perfused with 4% paraformaldehyde. For electron microscopy, 0.2% glutaraldehyde was added. Fifty micron thick sections were cut by vibratome in either the coronal or sagittal plane. Immunocytochemistry was performed using standard protocols, using diaminobenzidine (DAB) as the chromogen. Sections were stained with the monoclonal antibody MC1 (Ikonomovic et al. 1997, Jicha et al. 1997, 1999). Sections were post-fixed in 1% OsO4, dehydrated in ascending ethanol solutions, and embedded in epon-araldite. Thin sections were examined using a JEOL Jem 100 CX electron microscope.

Results

Generation of Transgenic Mice

Genomic mice. Eight tau-positive clones were isolated from the three libraries. Mapping analysis showed that only two clones, 30 and 32 from the PAC library contained the whole tau gene. These PACs were between 200 and 250 kb and contained all 14 exons, exon −1 and more than 7 kb of 5' flanking region, which includes the tau promoter. Further mapping in this area was not possible due to lack of available sequence data. Restriction maps of these clones in general agreed with published data (Andreadis et al. 1991) except that the region containing exons 10–14 was contained within one EcoRI fragment of >15 Kb and the 3' end (exons 10–14) is therefore shorter than published.

Injection of PAC 32 generated 102 pups. Two (lines 8c and 5d) were positive for the tau transgene, which was shown to be un-rearranged within the known coding and promoter area by PFGE and conventional gel mapping analysis. Subsequent protein analysis confirmed that the tau gene was functionally intact as both lines expressed trans-gene-derived tau at higher levels than endogenous protein. Densitometry showed that between 3–5 copies of the tau transgene were present in the genome.

Initial experiments were carried out with F1 and F2 offspring generated from (SWxB6D2F1) matings to founders. Overall, pup viability, adult heath and fecundity appear normal, although founder 8c died of unknown causes at 8 months of age. Founder 5d was sacrificed at 6 months and the oldest remaining transgenics are less than 9 months of age. The transgene transmits with Mendelian ratios and has shown stable transmission for four generations.

4R cDNA mice. Transgenic mice (line Alz17) that over-express a single isoform of human tau (tau40) were provided by Novartis Pharmaceuticals. Mice used for the study were bred on a hybrid background consisting of C57/blk6, DBA and Swiss Webster. The transgene consists of the human thy-1 promoter directing the expression of the longest 4R isoform (exon 10+, 2+, 3+) and contains 115 nucleotides of 3' UTR. This line is essentially similar to that described in Gotz et al. (1995) except that the transgene is expressed more uniformly throughout brain neurons and the level of tau40 protein is therefore higher.

RT-PCR analysis of tau transcripts. RT-PCR was used to compare splice variants in the brains of transgenic mice (lines 8c and 5d) with human brain variants. RT-PCR was performed using primers that spanned the alternately spliced exons 2, 3 and 10 and which were designed to be specific for human or mouse tau and for the identification of exon fragments based on their size. Primers that recognize exons 1 and 5 were used to distinguish between transcripts derived from the endogenous mouse gene, or the human transgene that contained one, two or no 5' inserts. In a similar way, primers to exons 9 and 11 were used to distinguish exon 10+(4R) transcripts from 10−(3R) transcripts derived from the mouse, or human tau.

RT-PCR showed that splicing of the human tau gene in the mouse is similar to the human brain in that all isoforms are represented. Splicing around exons 2 and 3 of the mouse and human gene is essentially identical and the ratio of 5' splice isoforms is maintained in mouse and human brain. Although both exon 10+ and 10− variant human RNAs are generated in the transgenic mouse, the ratio of these variants is different to the human brain, with the transgene-derived exon 10− (3R) variants being more highly represented. RT-PCR using mouse specific primers shows that the alternative splicing of the endogenous tau gene around exons 2, 3 and 10 is unaffected by the presence of the transgene as reflected in the relative levels of the different mRNA species.

ELISA assay. ELISA was used to determine the levels of human tau protein in the brains of non-transgenic and transgenic mouse lines and human cortex (Table 1).

The TG5 antibody recognizes both mouse and human tau. The data show that when normalized to endogenous levels of mouse, tau, line 8c, 5d and Alz17 mice have 3.7, 2.6 and 1.3 fold more total tau, respectively, than non-transgenic mice. Relative to 5d and Alz17, line 8c has 1.5 and 4 fold more total tau, respectively. The CP27 antibody specifically recognizes human tau. ELISA with this antibody showed that relative to 5 d and Alz17, line 8c has 1.4 and 2.8 fold more human tau, respectively. Thus, there is a good correlation between the levels of total and human tau between the lines. A second antibody that recognizes total tau (MN37) gave essentially identical results to TG5. In general, normal human cortex contained higher levels of human tau per mg total protein than hemi-brain samples from line Alz17, 5d or 8c, although the amount of tau in the human cortex samples varied widely, most likely due to post-mortem degradation.

Figure 2:
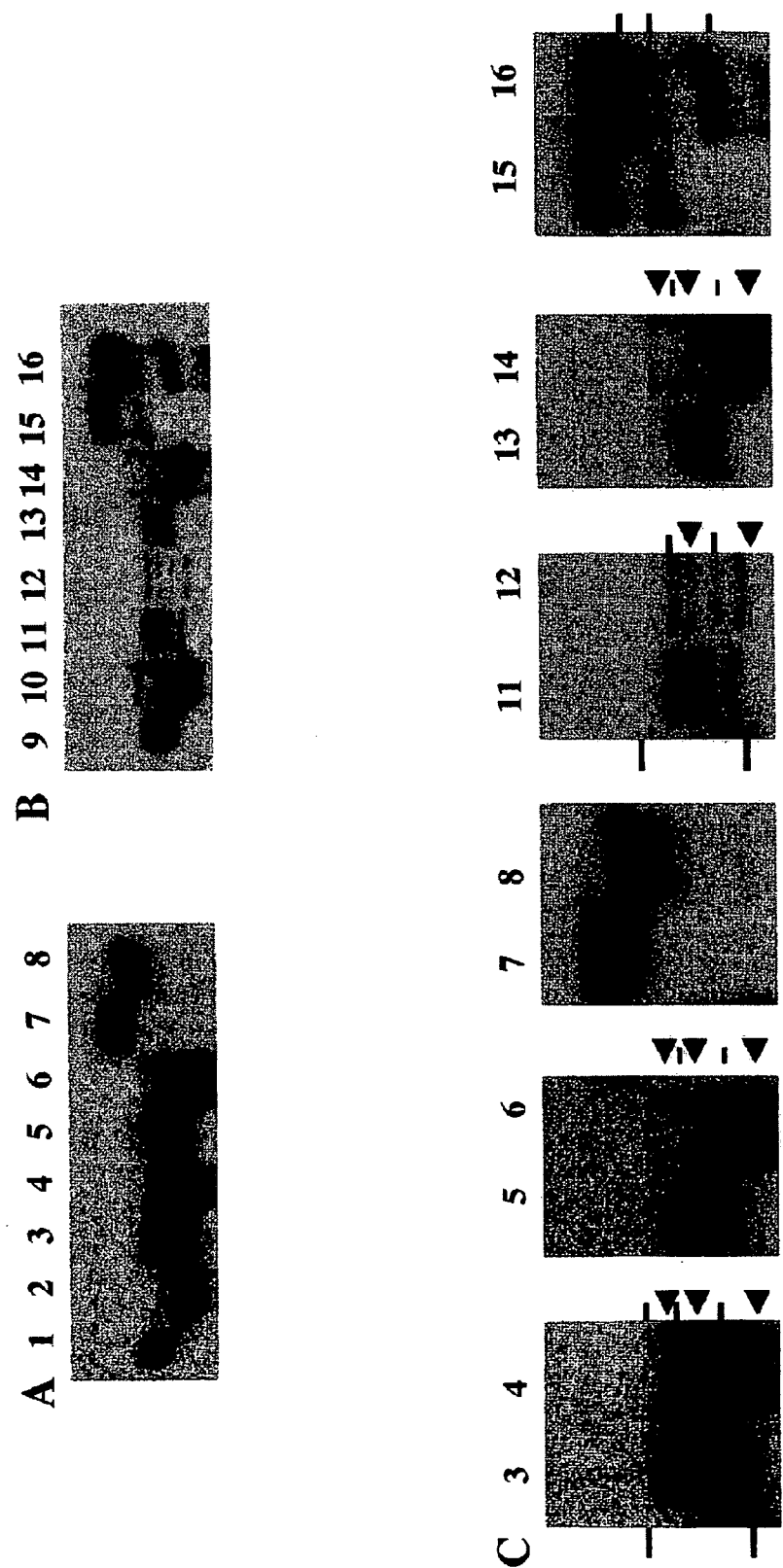
FIG. 2 is an immunoblot analysis of transgenic mouse lines expressing human tau. Blots were probed with human tau specified antibody CP27 (A) or an antibody (TG5) that recognizes both human and mouse tau (B). Lanes 1,3,5,7, heat stable tau from 5d, normal human cortex, 8c, and Alz17, respectively. Lanes 2,4,67,8, dephosphorylated tau from 5d, normal human cortex, 8c, and Alx17 line. Lanes 9,11,13,15 heat stable tau from 5d, normal human cortex, 8c, and Alz17, respectively. Lanes 10,12,14, and 16 dephosphorylated tau from 5d, normal human cortex, 8c, and Alz17, respectively. (C) An enlargement of the lanes from A and B. Thin lines indicate 4R isoforms, arrowheads indicate 3R isoforms. Thick lines represent the position of the 64 kDa (upper) and 46 kDa (lower) molecular weight markers. Exposure conditions for some samples were not within the linear range to allow the visualization of faint bands and the data is not intended to be quantitative.
Figure 3:
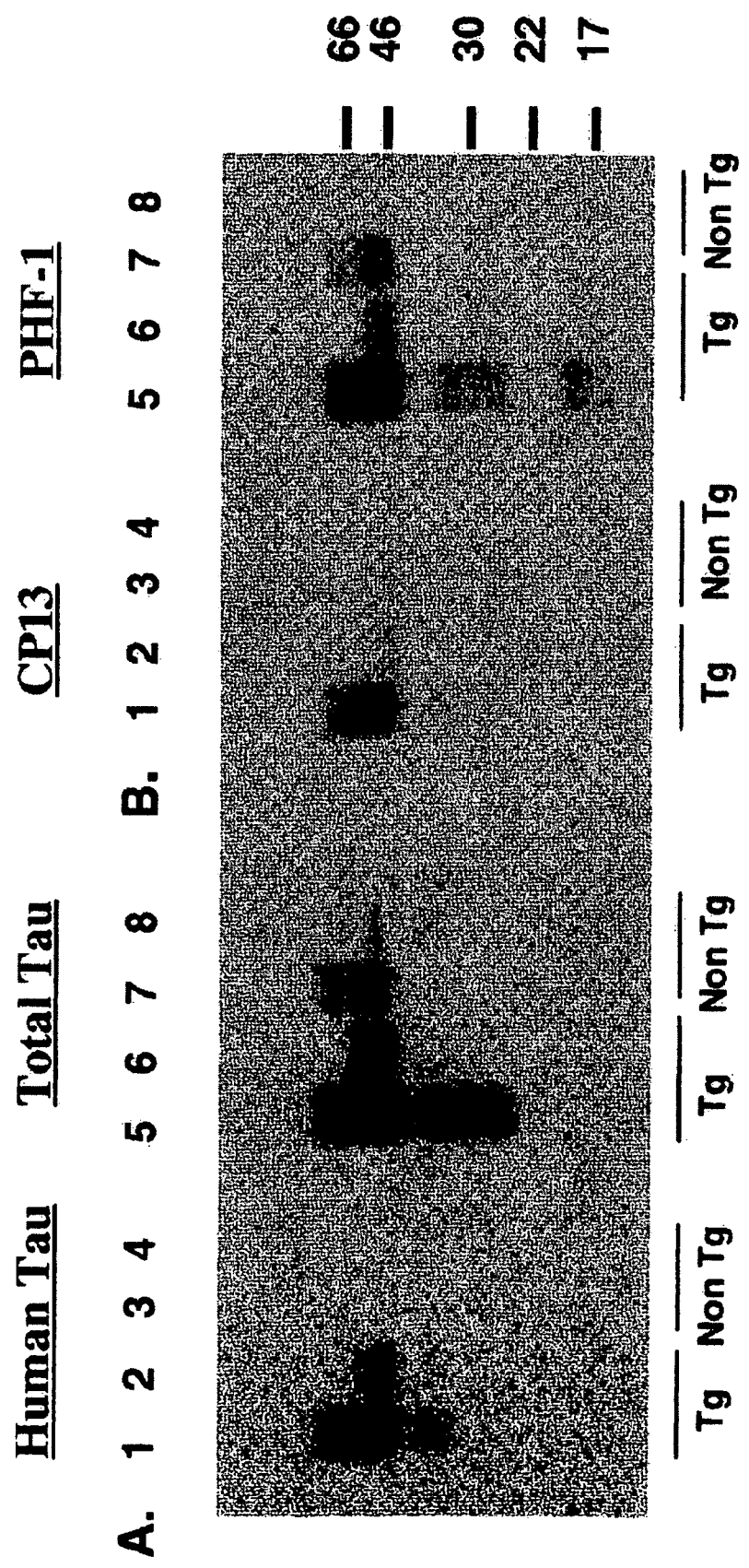
FIG. 3 is an immunoblot analysis of phospho-epitopes in transgenic line 8c. Blots prepared with soluble and pelleted tau from line 8c transgenic and nontransgenic mice were immunolabeled with phosphoindependent antibodies (CP27 and TG5, A) and phospho-dependent antibodies (CP13 and PHF-1,B). Lanes 1,2,5, and 6 are from transgenic mouse line 8c, lanes 3,4,7, and 8 are from a nontransgenic littermate. Lanes 1,3,5, and 7 contain soluble tau. Lanes 2,4,6, and 8 contain tau present in the SDS extracted pellet. Molecular weight markers are in kDa.
Figure 4:
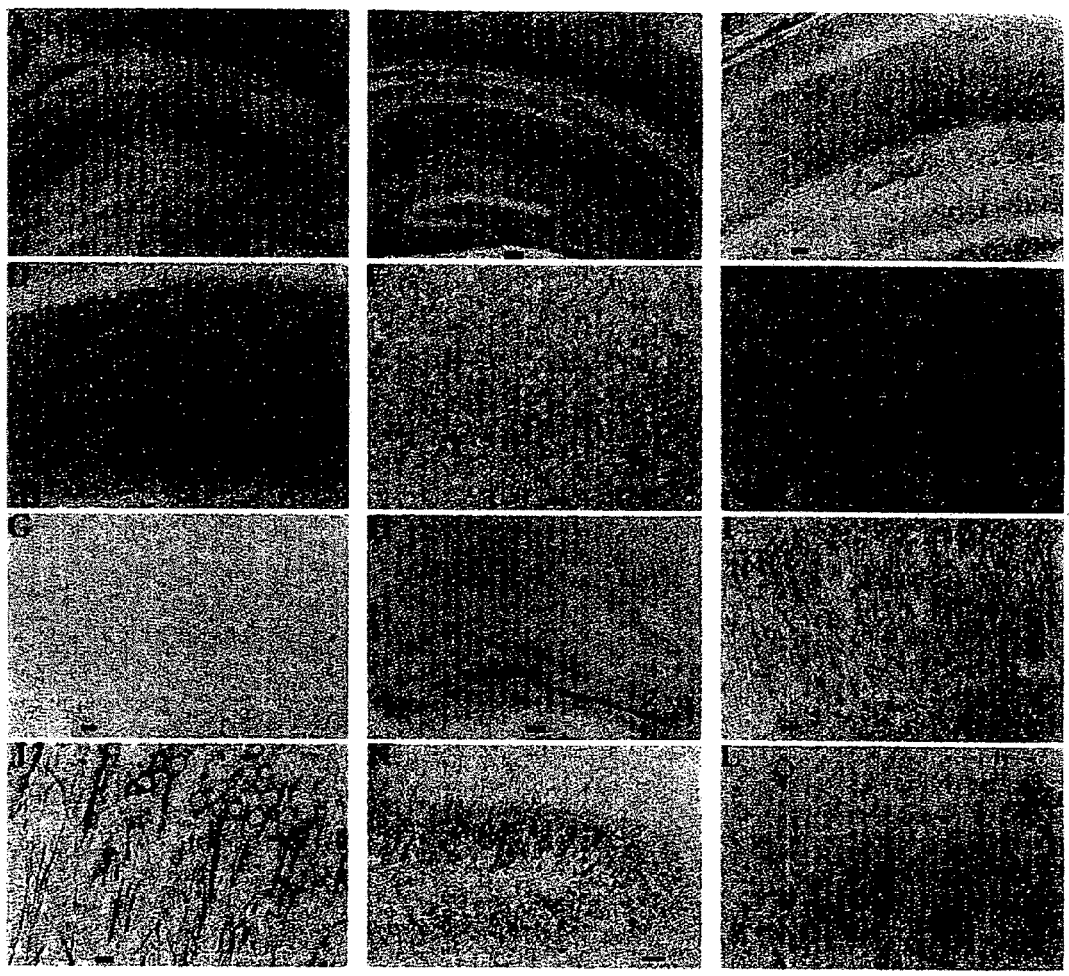
FIG. 4 is an immunohistochemistry with MC1 in the cortex and hippocampus. Immunolabeling of sections from genomic tau lines and Alz17 mice with MC1. (A) Low power view of hippocampus from genomic tau line 5d. (B) Hippocampus of the genomic tau line 8c. The higher power views in C and D show the fine diffuse staining of axon terminals in the outer two thirds of the molecular layer in line 8c. E and F are neocortex from line 8c showing the fine diffuse staining outlining the cell bodies of the large neurons, which are unstained. (B) Hippocampus of a representative nontransgenic mouse; (H) hippocampus from an Alz17 mouse. (I) Higher power view of the outer molecular layer, where staining is dominated by the large dendrites of the pyramidal cells. (J) Higher magnification showing somatodendritic staining is also evident in the denate gyrus, where many granule cells stain (K). (L) Some (but by no means all) cortical neurons show prominent somatodendritic staining. Scale bars: A, B, H=40 µm; C, G, I=12.5 µm; D, E, K=10 µm; F, J, L=4 µm.

Expression of tau isoforms in transgenic mice. To compare normal human tau proteins with those made in the transgenic mice, brain homogenates from the three transgenic lines and human cortex were analyzed by immunoblotting with tau antibodies TG5 and CP27 (FIG. 2). The human specific antibody CP27 recognized six tau proteins, ranging from 68 to 46 kD in dephosphorylated human cortex homogenate. Four major tau bands were clearly observed, and two minor bands were seen on longer exposures. These bands represent (from lowest to highest molecular weight) 3R 2−3−, 4R 2−3−, eR 2+3−, 4R 2+3−, eR 2+3+, and 4R 2+3+(sizing according to Spillantini et al. 1998). A similar pattern of tau proteins was observed in the dephosphorylated sample from the 8c and also line 5d. In the 8c homogenate, the lowest molecular weight protein (3R 2−3− isoform) was the most abundant. This correlates with RT-PCR data that shows that the 3R 2−3− transcript is likely the most abundant. All other isoforms were also represented in the 8c line. As expected, Alz17 synthesizes large amounts of the single human isoform, 4R 2+3+. Collectively, the data indicate that both the genomic and cDNA transgenic mice make human tau protein, and in the genomic tau mice, the full range of human isoforms are represented.

TABLE 1

Amount of tau present in transgenic mice and controls

| Line | Tau isoforms present | Mean amount of total tau/mg protein (SD) | Mean amount of human tau/mg protein (SD) |
|---|---|---|---|
| Non-transgenic (n = 4) | 4R mouse | 0.8 (0.09) | — |
| Human cortex (n = 5) | All human | — | 5.7 (1.7) |
| Genomic tau, 8c (n = 3) | All human + 4R mouse | 2.97 (0.09) | 2.55 (0.23) |
| Genomic tau, 5d (n = 3) | All human + 4R mouse | 2.15 (0.09) | 1.67 (0.02) |
| cDNA tau, Alz17 (n = 9) | 4R mouse + 4R human | 1.07 (0.03) | 0.63 (0.07) |

Tau phospho-epitope expression. Immunoblots of tau proteins in the soluble and pelleted fraction from 8c brain lysates were examined for the presence of phospho-epitopes using two antibodies, CP13 (serine 202) and PHF-1 (serines 396, 404) and compared to that in non-transgenic littermates. These blots were compared to identical blots probed with phospho-independent antibodies that recognize human tau (CP27) and total mouse+human tau (TG5). The majority of tau in the 8c mouse is present in the soluble fraction (lane A1), but a small amount is retained in the pellet fraction (lane A2), most likely as microtubule-associated tau. Extraction with sarcosyl removed the tau from the pellet, suggesting that appreciable levels of insoluble tau are not present in the brain. TG5 recognized both human and mouse tau. Phosphorylated tau epitopes recognized by both CP13 (analogous to AT8) and PHF-1 were more abundant in line 8c, suggesting that human tau is phosphorylated at these sites in the transgenic mouse brain, although it is not possible to determine at this stage if they are hyperphosphorylated.

Distribution of human tau in the brains of transgenic mice. The distribution of human tau in genomic tau mice compared to the 4R Alz17 line showed an overlapping, but distinctly different pattern, as visualized using the MC1 antibody. Line 8c (and to a lesser extent line 5d) showed intense staining in neuronal processes throughout the cortex and hippocampal formation. At higher power, the staining appeared to be punctate and to ring cell bodies suggesting a synaptic pattern of staining. The Alz17 line showed the same general pattern of tau distribution, but in contrast, showed strong somatodendritic staining which was particularly obvious in the pyramidal and granule layer neurons, and to a lesser extent in cortical neurons.

Figure 5:
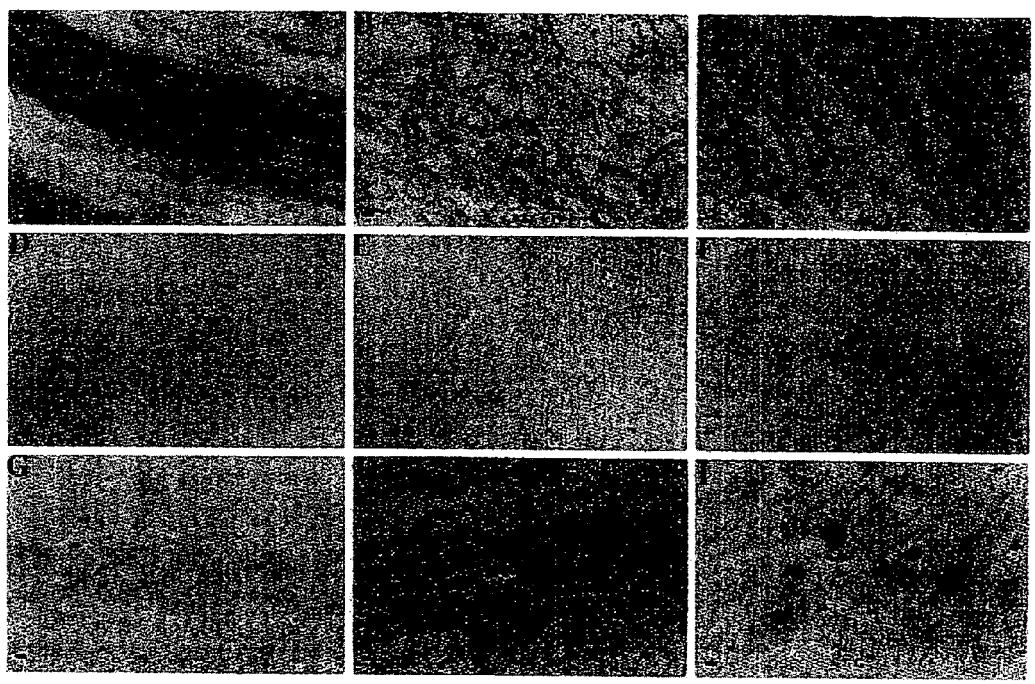
FIG. 5 is an immunohistochemistry with MC1 in other brain regions. Sections of genomic and Alz17 mice stained with MC1. (A) Corpus collosum from an 8c mouse showing clear axonal staining. (B) Striatum from an 8c mouse. As in other brain regions, there is no neuronal cell body staining, but dense bands of axons course through the striatum. (C) A similar pattern of staining is found in the striatum of the Alz17 mouse. (D) The cerebellum of the 8c mouse is essentially devoid of MC1 staining. (E) The cerebellum of the Alz17 mice show staining of numerous processes in the granule cell layer of the cerebellum, and essentially no staining in the molecular layer. (F) Very fine axonal staining in the spinal cord of the 8c mouse, which is difficult to demonstrate in the white matter of the cord. (G) Around motor neurons of the cord, a dense network of probable axonal processes was clearly evident. (H) In the Alz17 mice, some motor neurons were stained; these were less frequent in lumbar regions (not shown). (I) Throughout the cord of the Alz17 mouse, large axonal swellings were stained with MC1. Scale bars: 4 µm in all panels except D and E, where the bar is 12.5 µm.
Figure 6:
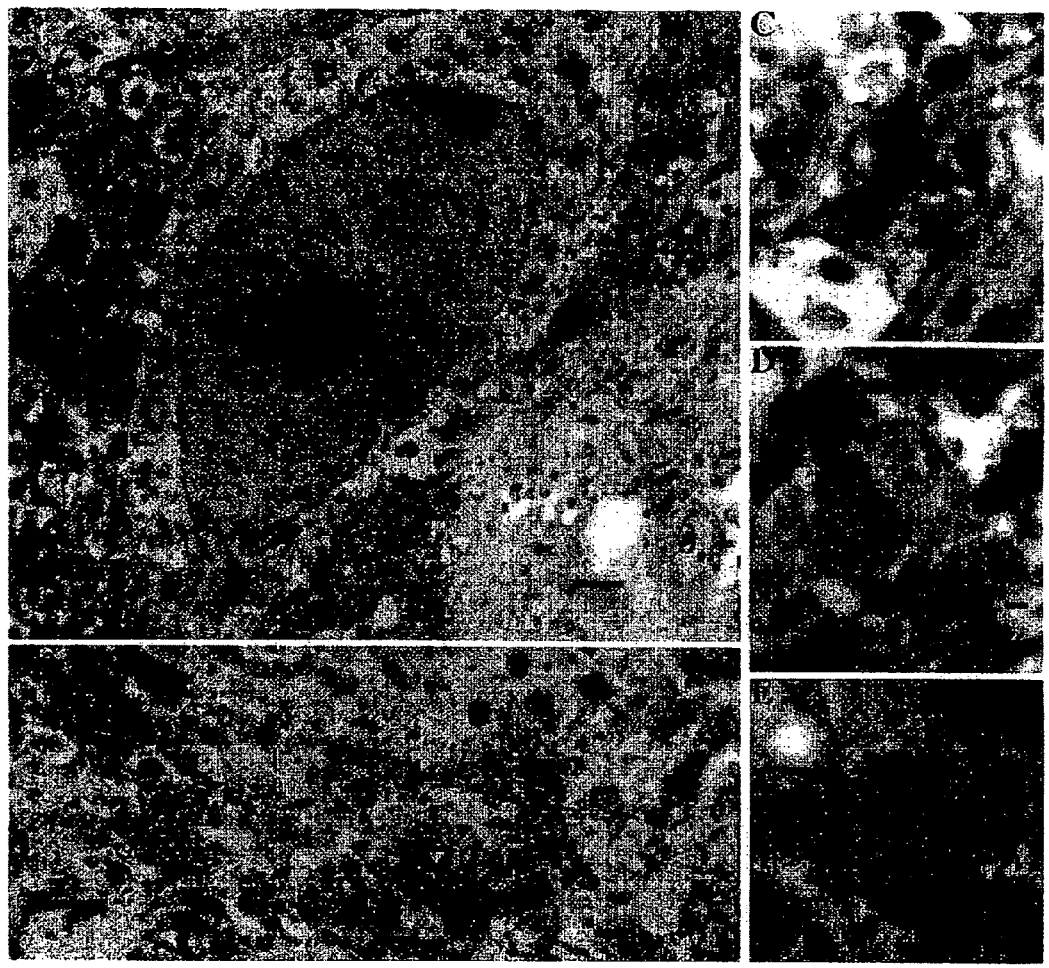
FIG. 6 is an electron microscopy of line 8c. Immuno-EM of MC1 stained hippocampus from the 8c line. (A) Large pyramidal neurons are unstained, but are surrounded by numerous stained synaptic structures, some of which are arrowed. (B) Higher power views of the pyramidal cell layer show numerous fine stained processes surrounding the cells. In C, D, and E, higher power views are presented of the staining of presynaptic terminals. The arrow is positioned in the postsynaptic element, pointing towards the synaptic thickening. Scale bars are 1 µm in A and B, 0.1 µm in C and D, and 0.2 µm in E.
Figure 7:
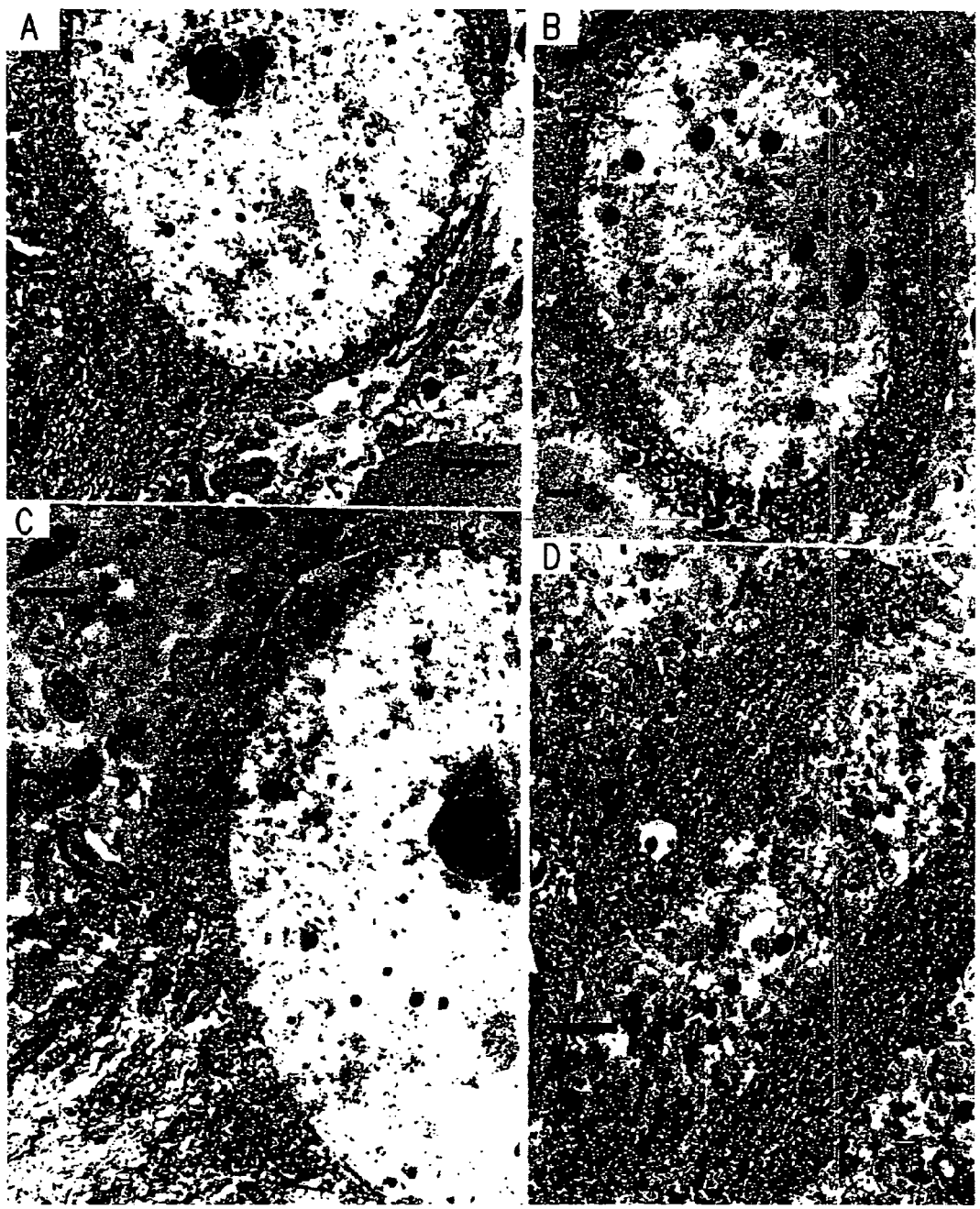
FIG. 7. Electron microscopy of line Alz17. Immuno-EM with MC1 in the hippocampus of the Alz17 mouse. (A–C) Pyramidal cells show dark cytoplasmic staining with MC1, although unstained cells are also visible. The staining is diffuse in the cytoplasm, with no evidence of filamentous staining or bundles of stained filaments. (D) Some of the atypical denrites of the pyramidal cells are darkly stained, again with no evidence for aggregation of staining. Scale bars: 1 µm.
Figure 8:
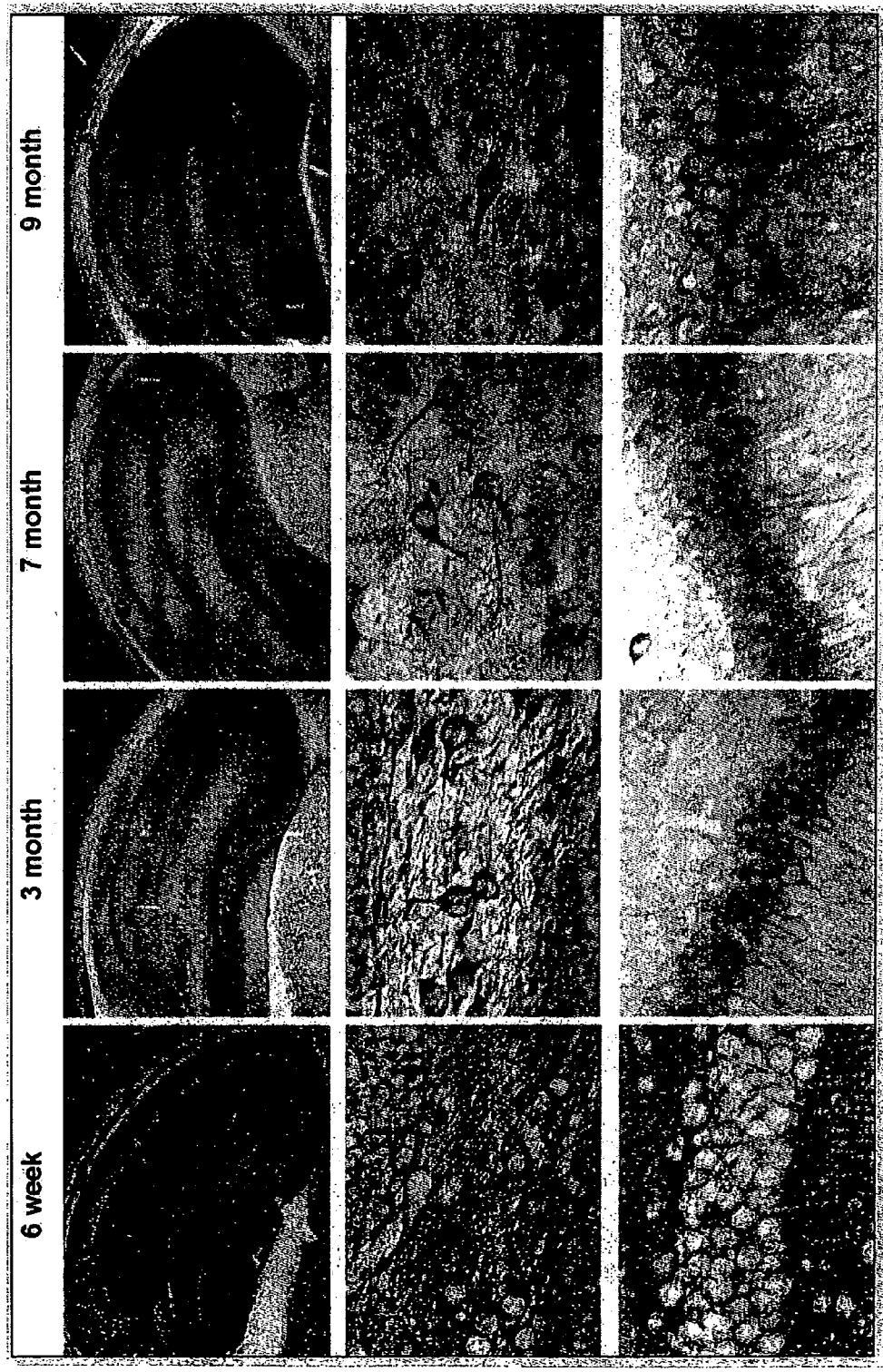
FIG. 8. CP13/AT8 (phospho ser 202) staining in hTau (genomic/tau null) mouse hippocampus during development (6 weeks, 3 months, 7 months, and 9 months).
Figure 9:
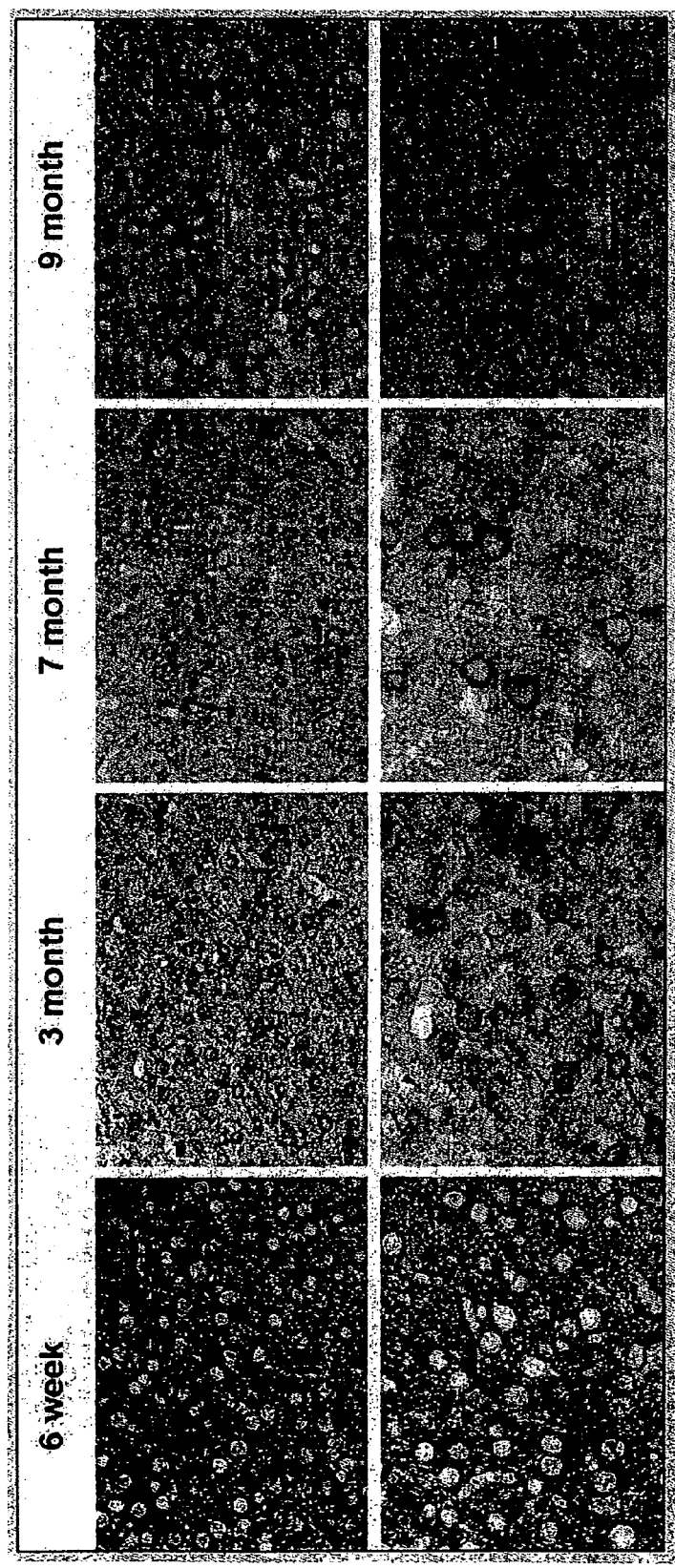
FIG. 9. CP13/AT8 (phospho ser 202) staining in hTau mouse cortex during development (6 weeks, 3 months, 7 months, and 9 months).
Figure 10A:
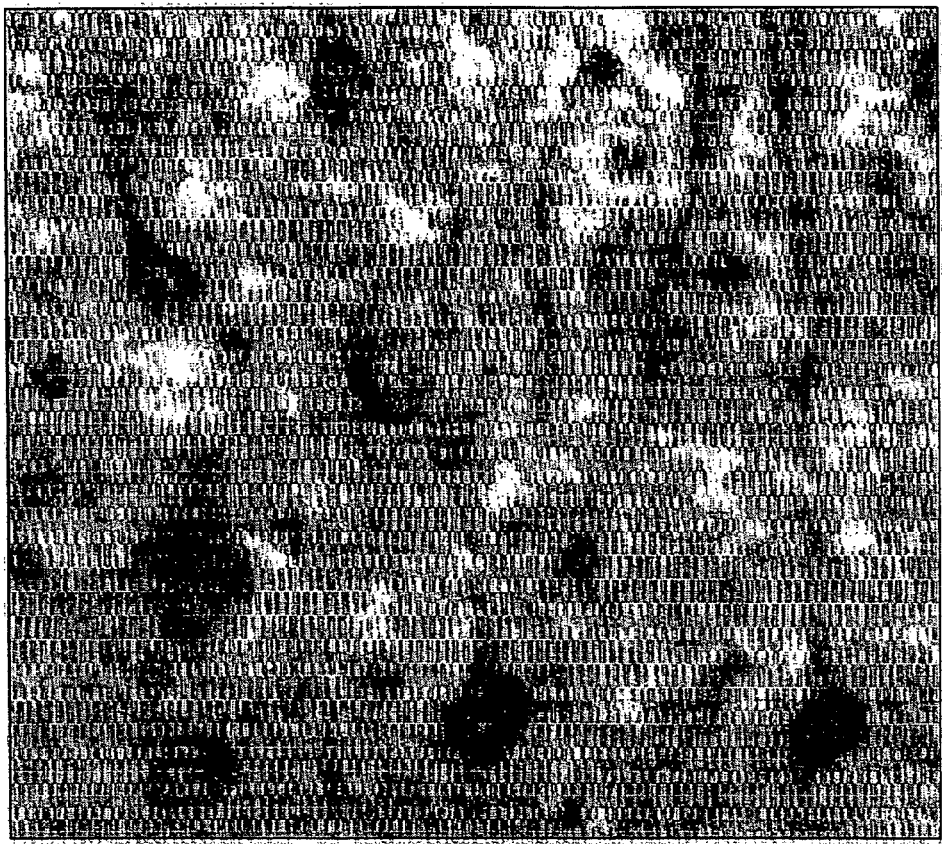
FIG. 10. TG3 (phospho/conformation specific) staining in cortex of hTau mice.
Figure 10B:
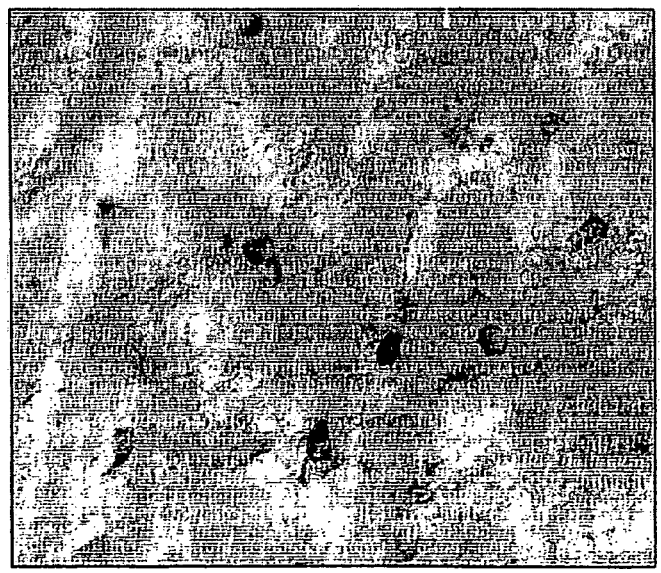
Figures 1, 11:
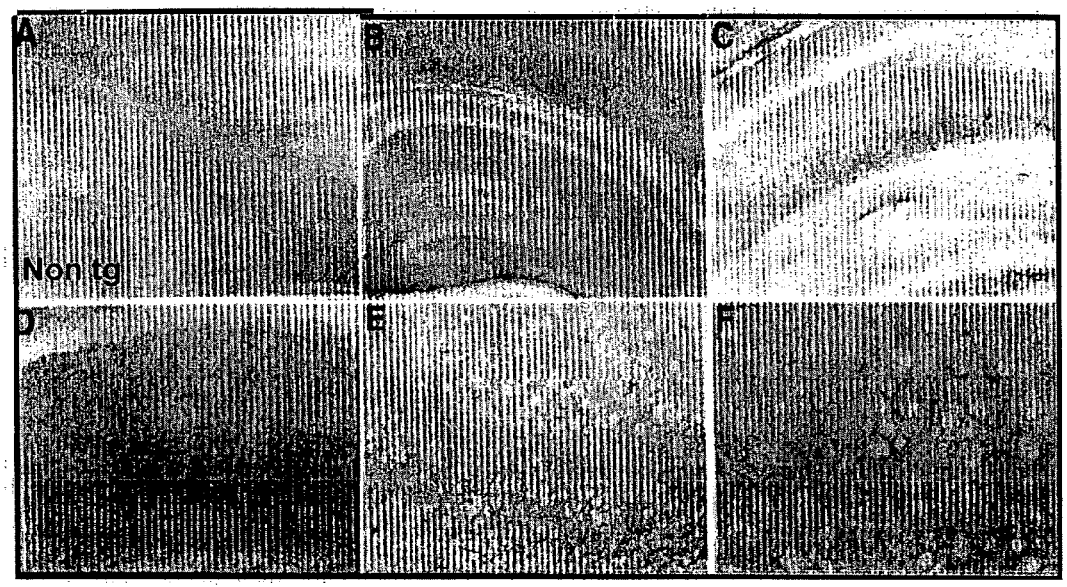
FIG. 11. MC1/Alz50 (conformational specific) staining in hTau mouse brainstem.
Figures 2, 11:
Figure 12A:
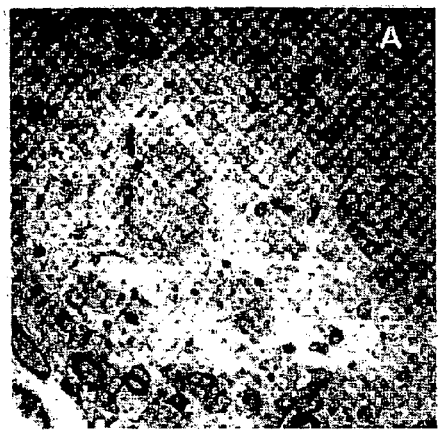
FIGS. 12A–D. (A) (B) (C) Cell body filaments. (D) Proximal dendrite filaments.
Figure 12B:
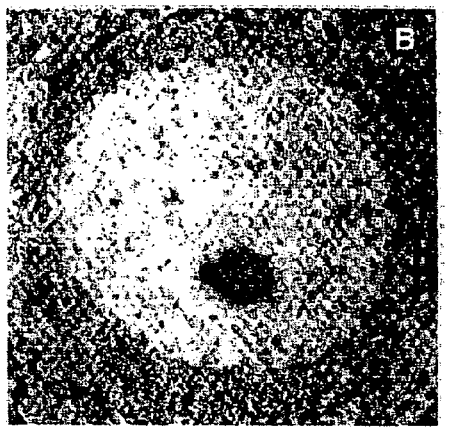
Figure 12C:
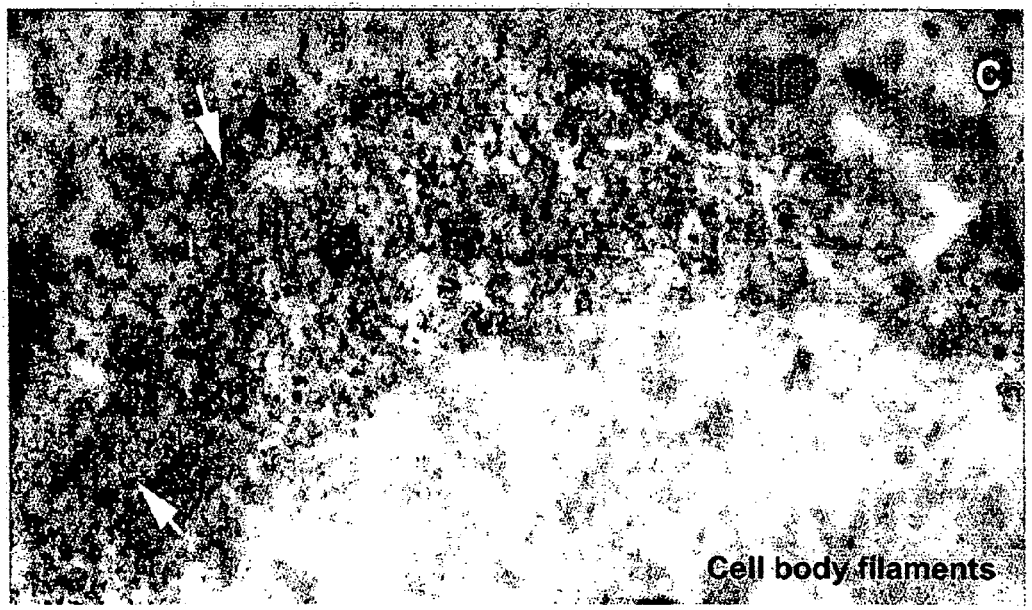
Figure 12D:

Tau immunoreactivity was seen in both grey and white matter indicating clear axonal staining which was particularly evident in the 8c mouse (FIG. 5a). Regions such as the striatum, had a similar distribution of human tau in 8c and Alz17 mouse brain. Other regions, notably the cerebellum and spinal cord were less similar. The cerebellum of the 8c mouse was devoid of staining whereas some staining was seen in granule cell layer processes in the Alz17 mouse. In 8c mice, very fine axonal processes in white matter of the spinal cord were faintly stained, but motor neuron cell body staining was not seen. In contrast, the Alz17 mouse showed some staining of motor neuron cell bodies in the cord, and also the presence of tau-immunoreactive swellings. These swellings also stained positively with antibodies to neurofilaments, confirming their axonal character. The presence of abnormal structures in the spinal cords of these mice correlated with the development of a hind-limb clasping phenotype that could be observed when both hemizygous and homozygous Alz17 mice were picked up by the tail. This phenotype was especially obvious in mice between 6–12 months of age. No motor abnormalities or abnormal pathology has been observed in the spinal cords of 8c or 5d mice up to 8 months of age.

Immuno EM using MC1 showed that in 8c mice, neuronal cell bodies in cortex and hippocampus were unstained but were surrounded by numerous stained synaptic structures. Human tau was localized both in neurites and at synaptic terminals. In Alz17 mice, human tau was found in the cytoplasm and neurites of many cells, although some cells remained unstained. Cytoplasmic staining was diffuse with no evidence of filamentous staining or bundles of stained filaments. Overt aggregation of the tau was also absent in darkly stained apical dendrites. In the Alz17 mice, tau was not found in synaptic structures.

Discussion

The biology of tau and its contribution to human neurodegenerative disease can be explored in transgenic mouse models that express different human tau isoforms. As described hereinabove, transgenic mice were prepared that over-express a human tau genomic transgene and several differences were noted between genomic human tau transgenic mice and mice over-expressing a single isoform of the longest human tau protein.

Analysis of splice variants in the genomic mouse lines 8c and 5d shows that mice are capable of making all six isoforms of human tau and that the cis-activating splice regulators in the human tau gene that govern splicing events around exons 2, 3 and 10 are functional in mouse (Grover et al. 1999). Although all six isoforms are generated in the mouse, it is interesting to note that the ratio of 3:4 repeat human tau derived from the human gene differs as relatively more 3-repeat containing human tau is present in mouse brain compared to human. The reason for this shift is unknown, but it is likely to be a carefully regulated mechanism as both positive and negative trans-acting factors regulate exon 10 alternative splicing in humans (D'Souza et al. 1999). At the protein level, all isoforms are represented, but the 3 repeat isoforms (3R2–3– especially), are more abundant than in human brain, which confirms that the ratio of mRNA splice variants in the transgenic mice is maintained after translation. Overall, the representation of human tau isoforms in mouse brain tissue is very similar to that seen in human brain except that 3R tau is more abundant.

The MC1 antibody recognizes an epitope of tau that was isolated from human AD brain, and it is specific for human tau in an abnormal conformation (Ikonomovi et al., 1997, Jicha et al., 1997, 1999). MC1 recognizes the human tau in all the transgenic lines studied suggesting that over-expression of normal tau isoforms leads to a conformation change in the derived tau protein. Although it is likely that the conformational change that allows us to visualize the human tau in the transgenic mice is a fortuitous artifact of over-expression, it is also possible that pathogenic tau is forming in the mice, and general MC1 immunoreactivity reflects an early stage that has perhaps not been identified in post-mortem brain tissue from patients with late-stage disease. A second antibody, TG3, is also specific for tau in AD brain (Jicha et al. 1997), but at the ages studied, this antibody was negative in the transgenic mouse brain. Other antibodies (e.g., PHF-1, CP13/AT8, and TG5) also recognize endogenous mouse tau and are not informative by immunohistochemistry.

Mice such as Alz17 that have elevated human 4R tau could be considered a model for FTPD-17 where splice site mutations shift the normal 1:1 ratio of 3:4 repeat tau in favor of more 4R tau (Spillantini et al. 1998, Hong et al. 1998, Godert et al. 1999). As these mutations are associated with neurodegeneration and dementia, mice with elevated 4R tau could also be expected to develop a degenerative phenotype. Although detailed cell counts were not performed, there is no overt neurodegeneration in the Alz17 lines up to 18 months of age. However, both Alz17 mice and another 4 repeat cDNA mouse (J. Turner, pers. commun.) display a subtle hind-limb clasping phenotype when picked up by the tail. Examination of spinal cord from Alz17 showed the presence of abnormal tau and neurofilament immunoreactive axonal swellings in transgenic, but not in age-matched non-transgenic mice. A few abnormal spheroids were also visualized in other regions of the brain but they were immunoreactive only with anti-neurofilament antibodies and not with MC1. The abundance of tau containing spheroids in the spinal cord suggests that this region might be particularly sensitive to tau abnormalities which is perhaps significant given the association of spinal cord pathology and amyotrophy with some tauopathies (Lynch et al. 1994, Spillantini et al. 1997, Zhou et al. 1998).

In comparison to the cDNA mice, hind-limb clasping and spinal cord abnormalities were not observed in the genomic mice at ages up to eight months (oldest age studied). However, Alz17 mice differ from the genomic lines in several respects; they have greatly elevated levels of 4R, 3+2+tau, they show disrupted neurofilament staining, the level of tau immunoreactivity in the spinal cord is higher than in the genomic mice and they show somatodendritic distribution of the human tau protein in many neurons. The influence of background strain on the phenotype in Alz17 mice is not considered to be significant however as Alz17 mice crossed onto the genomic line background (Swiss Webster/B6/DBA) show essentially the same phenotype as parental strain Alz17 mice (C57/blk6).

Somatodendritic staining has been shown in several lines of tau cDNA mice, which include a different 4R, 2+3+ line (Gotz et al. 1995) and a 3R, 2–3– line (Brion et al. 1999) but was not observed in the genomic mice. One possible difference between the cDNA mice and genomic lines is the inclusion of a longer 3' UTR sequence in the latter as sequences in the 3' UTR have been shown to affect cellular distribution of tau in the rat (Behar et al. 1995, Aranda-Abreu 1999). As changes in tau distribution from axonal to somatodendritic are one of the early features in AD tau-pathogenesis (Braak et al. 1993; Kosik et al. 1989), the presence of tau in the 'abnormal' (somatodendritic) compartment in some cDNA mice may either enhance the utility of the model, or may obscure essential pathogenic trafficking events. Thus, mouse lines with different tau transgenes will be useful to study the biology of tau in vivo, and to generate suitable animals for disease modeling.

EXAMPLE II

Characterization of a Mouse Line That Expresses Only Human Isoforms of Tau

Tau is a microtubule associated protein (MAP) that is enriched in neurons. The microtubule binding domain of tau is composed of either three or four variable repeats (3R or 4R) depending on the presence or absence of exon 10. Tau in adult mouse is exclusively 4R, whereas tau in normal human brain is a balance of 3R and 4R. The ratio of 3R to 4R is shifted in some neurodegenerative diseases, including Fronto-Temporal Dementia and Parkinsonism linked to Chromosome 17. In the process of tangle formation, tau is abnormally hyperphosphorylated, re-localizes from the axon to the neuronal cell body, aggregates into filaments and ultimately into neurofibrillary tangles. Changes in tau distribution from axonal to somatodendritic are one of the early features of the tauopathy associated with Alzheimer's disease.

A transgenic mouse line that expresses only human isoforms of tau has been generated by mating a mouse that expresses all isoforms of human tau (8c) in addition to mouse tau (Example I) with a knock out mouse that does not express mouse tau. These mice (hTau mice) show somatodendritic staining of some neurons with MC1, an antibody specific for tau in an abnormal conformation. The 8c mouse also showed reactivity with MC1, but staining was diffuse and limited to axons.

As hTau mice show an accumulation of abnormal tau in the cell bodies and dendrites of neurons in the hippocampus, neocortex and brainstem by 3 months, which increases with age, tau in hTau mice is reactive with antibodies that are specific to phosphorylation and conformation changes associated with Alzheimer's disease, including: phosphorylation at S202 and T231, and the MC1 conformation (FIGS. 8–11), and insoluble filamentous tau accumulates in the dendrites of hippocampal neurons in these mice, hTau mice recapitulate many of the early events in tangle formation associated with Alzheimer's disease.

Moreover, while other groups have generated transgenic mice that develop tangles, all of those mice expressed mutant tau and/or did not develop the spatio-temporal distribution of tangles characteristic of disease. In contrast, the results presented herein, including the finding that tau can become filamentous and deposited in the absence of mutation, suggest that the tau pathology observed in the hTau mice is the result of an altered ratio of tau isoforms, and that this could also be significant for the development of tau pathology in Alzheimer's disease.

EXAMPLE III

Organotypic Slice Cultures from Transgenic Mice as Disease Model Systems

For most researchers, the cost of maintaining transgenic mice and screening drugs in them is prohibitively high, and competition for cage space limits their availability in animal facilities. Alternatives to whole animal models include the use of cells transfected with the gene of interest, or the use of primary cultures or organotypic slices from relevant transgenic mice. The creation of a transfected cell model involves the choice of one type of cell to be either stably or transiently transfected with the DNA encoding the protein of choice. The cell type chosen is usually of one kind (neuronal, astroglial, etc.), and prior to transfection, the cell has been immortalized through the introduction of the Epstein Barr virus. Expression vectors often use promoters (such as that derived from CMV) that lead to high levels of constitutive expression, which can overload cellular machinery leading to inappropriate trafficking or metabolism of the target protein or other cellular processes. Despite these drawbacks, transfected cells have been used successfully for decades to investigate the function of new proteins although reported data is often later identified as artifactual.

The use of primary cultures has recently become more popular. Primary cultures usually consist of mixed cell populations derived from homogenization of fetal tissue. Primary cells can grow in culture for a limited time, and often the cultures become overgrown with cells of one type, especially glia. They can, however, be prepared from specific areas, for example the brain cortex which may be important if the function of the protein of interest is regionally regulated. If the tissue is derived from a transgenic mouse, further manipulation of the cells to express the protein of interest is not required, but some of the same problems caused by over-expression artifacts apply to cultures of cells from transgenic mice as for transfected cells. Often though, the promoter used in a transgenic does not express at such a high level as those used in the most frequently used expression vectors. Also, if the mice have been genetically engineered by targeting to generate a knock-in or knock-out mouse, overexpression artifacts are not an issue. Transfection of primary cultured cells is very difficult, so primary cultures from nontransgenic mice are usually used for cell biology studies. Despite their advantages over transfected cells, mixed primary cultures still do not model the intact adult brain well as cells are maintained as a monolayer, connections between cells have been disrupted, and components such as the vascular system are missing.

The most physiologically relevant ex vivo model system is obtained through the creation of organotypic slice cultures. Organotypic cultures provide a unique system in which to examine integrated brain physiology including synaptogenesis, or cell dysfunction, death or pathology development linked to aging or simulated pathogenic conditions. Long-term slice cultures from the hippocampus are particularly valuable in this regard as they retain the mechanisms responsible for synaptic plasticity (e.g., long-term potentiation) and responsiveness to pathological insults (e.g., excitotoxicity) (for a review see Bahr 1995). Slices can be prepared from the second postnatal week of development, and they display a number of relatively mature features that continue to develop and be maintained over succeeding weeks to months.

Use of ex vivo slices to study the pathogenesis of tauopathy.

Mouse models. Transgenic mouse models overexpressing tau transgenes have been created. Mice over-expressing a mutant tau transgene (line P301L) develop pretangles and AD-type tangles mainly in hindbrain and spinal cord (Lewis et al. 2000). Transgenic mice over-expressing the human, wild type genomic sequence of tau (line 8c) do not develop pretangles, but show a normal distribution of the six isoforms of tau in axons throughout the body, and in the periphery (Duff et al. 2000). Mice expressing the genomic sequence were crossed to a tau knockout line to generate a mouse with human tau only (line hTau). These mice initially have the same tau distribution as the parental 8c line (i.e., axonal), but by 12 weeks of age, the distribution has shifted to somatodendritic distribution that resembles the earliest stages of AD tauopathy (see chapter by Davies et al. for complete description).

Figure 13:
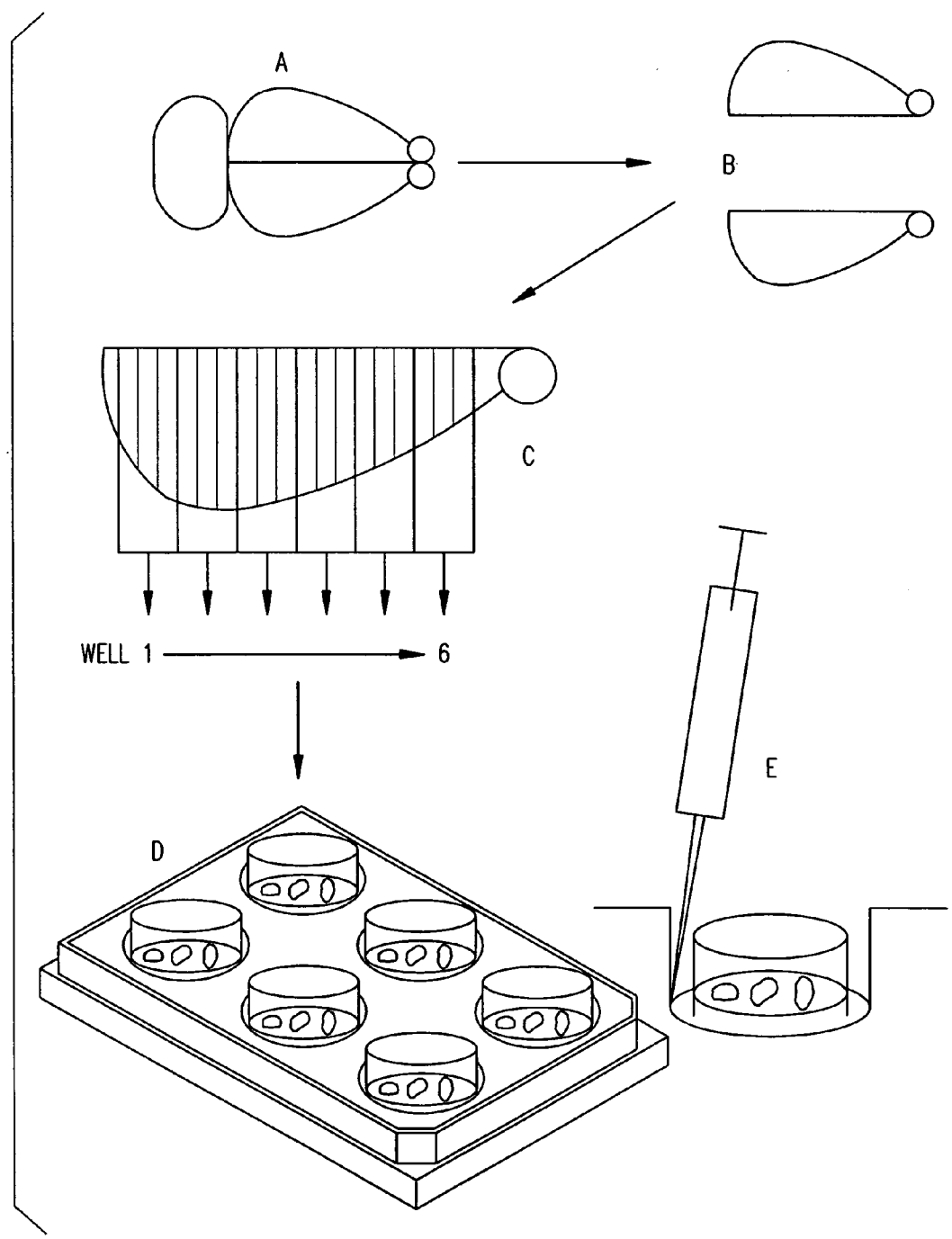
FIG. 13. Procedure overview. Brains from mice at p11–13 (A) are divided into hemispheres (B). Hemibrains are sliced into slices at a thickness of approximately 400 μm either coronally (C) or sagitally, and three slices are placed on a culture medium, in, for example, a 6 well plate (D). Slices were transferred to membrane inserts (Millipore; Bedford, Mass.) and grown without reperfusion in media containing 25% serum, according to a protocol modified from Bahr (Bahr et al. 1995). Media is fed from the bottom of the culture every 2 days (E). Experimental agents can be introduced either through addition to the media, or they can be added drop-wise to the surface of the culture.

Preparation of slices and assessment of viability. Slice cultures were prepared from four lines of transgenic mice: non transgenic, tau 8c, hTau and P301L. Eighteen 400-μm thick slices were obtained from each hemi brain, i.e., two 6-well plates of complete consecutive slices (3 slices/well) were obtained from one mouse brain at p11–13 days of age. Slices were transferred to membrane inserts (Millipore; Bedford, Mass.) and grown without reperfusion in media containing 25% serum, according to a protocol modified from Bahr (Bahr et al. 1995). Media is fed from the bottom of the culture every 2 days. Experimental agents can be introduced either through addition to the media, or they can be added drop-wise to the surface of the culture (FIG. 13). Immediately after preparation, slices are white, but within 14 days, they had turned from white to transparent. Brain weight from each hemi brain at p11 is 103±10 mg (mean±SD, n=6).

Figure 14:
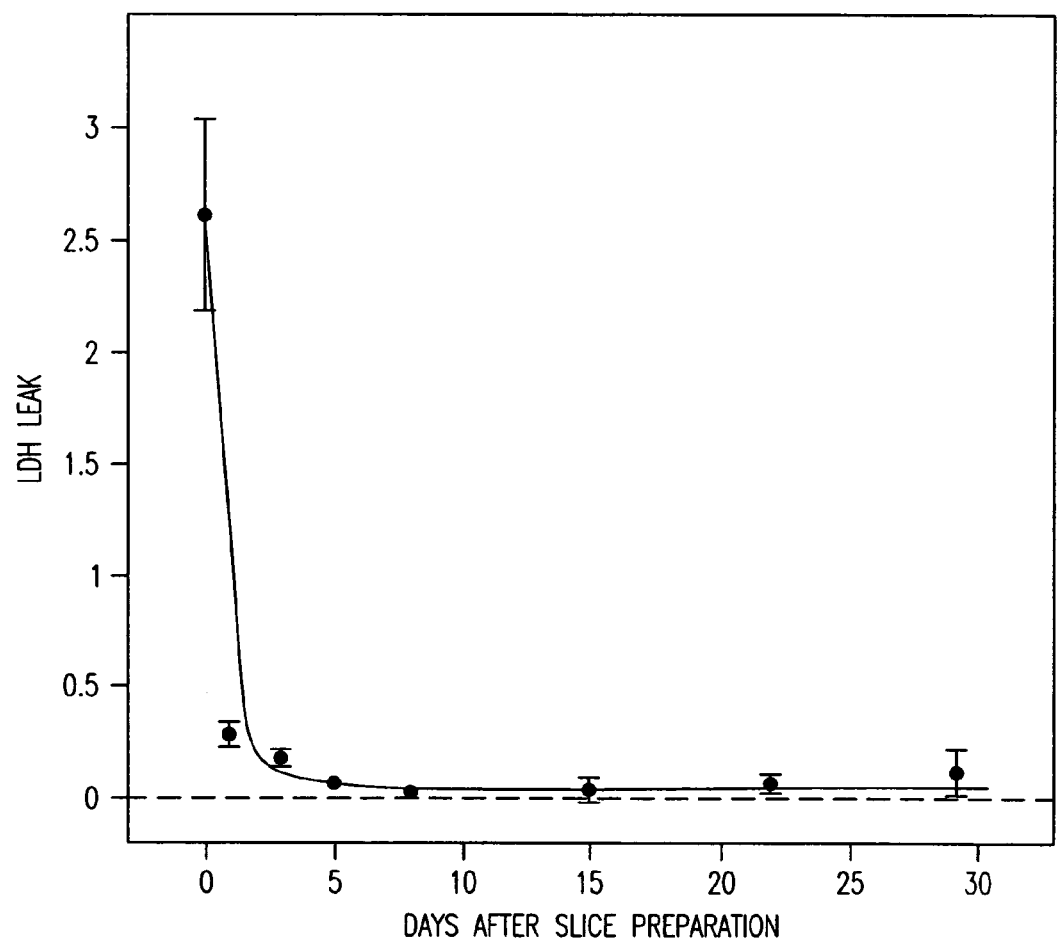
FIG. 14. Viability assessment by LDH leak assay. LDH level in medium that had been cultured with slices for 3 hours was compared. LDH levels in medium increased immediately after slice preparation, and then quickly returned to the control level 2 days after preparation. After 5–10 days, the slices stabilize and they can be maintained in culture for up to 6 months.

LDH is a stable cytoplasmic enzyme present in all cells that is rapidly released into the culture medium upon damage of the plasma membrane, thus LDH leak to the medium is a marker for cell damage. LDH level in medium that had been cultured with slices for 3 hours was compared. LDH levels in medium increased immediately after slice preparation, and then quickly returned to the control level 2 days after preparation (FIG. 14). MTT converts to formazan, which gives a purple coloration in living cells. Almost the entire (95%) transparent slice from p11–13 day old slices changed to purple after incubation with MTT. Slices from older mice were prepared, but the colored area represented only 60%, 20% and <10% of slices cultured from 6 week-old, 9 week-old and 6 month-old mice, respectively. Once slices from 2 week-old mice had changed to transparent, they could be maintained for up to 6 months in culture.

Formation of abnormal tau in slices. Slices were removed from culture at 2 week intervals after the two week stabilization period. Slices from P301L and 8c mice were initially examined at 4 weeks in vitro (wiv), then at 6, 8, 10, 16 and 24 wiv. Slices from hTau mice were examined at 4 and 16 wiv. Slices were removed from membranes and fixed in 4% PFA. They were then immunolabelled by standard immunohistochemical procedures. Antibodies used included MC1 (Jicha et al. 1997) which recognizes tau in an abnormal conformation usually associated with AD tangles. Neurons prepared from non-transgenic mice failed to show staining with MC1 at any age studied (up to 24 wiv) (FIG. 15A). Slices from 8c mice developed immunoreactive tangles only in the oldest cultures (24 wiv) (data not shown). Slices from P301L and htau mice however, developed MC1 immunoreactive tangles at the earliest stage examined (2 wiv), FIGS. 15B–C). P301L slices did not appear to develop more pathology with longer culture times, but immunoreactive neuron numbers in htau cultures did appear to increase progressively in the early weeks of culture. Immunoreactive neurons were represented throughout the cortex. Both the cell bodies and processes of neurons were immunolabelled, and neurons of all types (uni, bi and multipolar) were represented.

Use of slices in drug studies. As slice cultures retain many of the features of the intact brain, they have potential as model systems for the testing of agents predicted to exacerbate, or ameliorate disease pathology. It should be remembered, however, that ex vivo conditions are very stressful to living cells regardless of whether they are immortalized, transfected cells, primary cultures or organotypic slices. Culturing slices induces the activation of numerous pathways including the immune and inflammatory response, and stress responses including abnormal phosphorylation of a variety of proteins. Thus, the action of exogenous agents will be in addition to stimuli already active on cellular processes, which may confound results. The greatest utility for slice cultures so far is in evoking pathology such as amyloid formation in APP over-expressing mouse slices (data not shown), tau pre-tangle type pathology in slices from tau transgenic mice (as shown in FIG. 15), and Lewy body type pathology in slices from a-synuclein over-expressing mouse slices (data not shown). Tau slices are currently being examined to determine how potentially pathogenic agents, such as overactive kinases, or possible therapeutic agents, such as kinase inhibitors, may be used to study pathogenic pathways that lead to tauopathy.

CONCLUSION

Organotypic slice cultures have been prepared from the brains of transgenic mouse models of AD-type pathology. Cell types within the slice undergo differentiation and slices can be maintained in culture for up to 6 months when prepared from young neonates. Slices have been prepared from mice over-expressing genes of relevance to Alzheimer's disease including mutant or wild type tau. Neurons in these slices develop pretangles that are immunoreactive for a number of markers of abnormal tau. Organotypic slice models are currently being used to test the impact of tangle enhancers or inhibitors as a prescreen for efficacy before testing drugs in vivo.

REFERENCES

Andreadis, A., Brown, W. M., Kosik, K. S., Structure and Novel Exons of the Human Tau Gene, *Biochemistry*, 31:10626–33 (1992).

Aranda-Abreu, G. E., Behar, L., Chung, S., Furneaux, H., Ginzburg, I., Embryonic lethal abnormal vision-like RNA-binding proteins regulate neurite outgrowth and tau expression in PC12 cells, *J. Neurosci.* 19:6907–17 (1999).

Bahr, B., Long—term hippocampal slices: a model system for investigating synaptic mechanisms and pathologic processes, *J. Neurosci. Res.*, 42:294–305 (1995).

Bahr, B. A., Kessler, M., Rivera, S., Vanderklish, P. W., Hall, R. A., Mutneja, M. S., Gall, C., Hoffman, K. B., Stable maintenance of glutamate receptors and other synaptic components in long-term hippocampal slices. *Hippocampus*, 5:425–39 (1995).

Behar, L., Marx, R., Sadot, E., Barg, J., Ginzburg, I., Cis-acting signals and trans-acting proteins are involved in tau mRNA targeting into neurites of differentiating neuronal cells, *Int. J. Dev. Neurosci.*, 13:113–27 (1995).

Braak E, Braak H, Mandelkow E M., A sequence of cytoskeleton changes related to the formation of neurofibrillary tangles and neuropil threads, *Acta Neuropathol (Berl).*, 87:554–67 (1994).

Brion J P, Tremp G, Octave J N., Transgenic expression of the shortest human tau affects its compartmentalization and its phosphorylation as in the pretangle stage of Alzheimer's disease, *Am J. Pathol.*, 154:255–70 (1999).

Dayanandan R, Van Slegtenhorst M, Mack T G, Ko L, Yen S H, Leroy K, Brion J P, Anderton B H, Hutton M, Lovestone S., Mutations in tau reduce its microtubule binding properties in intact cells and affect its phosphorylation, *FEBS Lett.*, 446:228–32 (1999).

D'Souza I, Poorkaj P, Hong M, Nochlin D, Lee V M, Bird T D, Schellenberg G D., Missense and silent tau gene mutations cause frontotemporal dementia with parkinsonism-chromosome 17 type, by affecting multiple alternative RNA splicing regulatory elements, *Proc. Natl. Acad. Sci. USA.*, 96:5598–603 (1999).

Duff, K., Knight, H., Refolo, L. M., Sanders, S., Yu, X., Picciano, M., Malester, B., Hutton, M., Adamson, J., Goedert, M., Burki, K., Davies, P., Characterization of pathology in transgenic mice over-expressing human genomic and cDNA tau transgenes, *Neurobiol. Dis.*, 7:87–98 (2000).

Goedert M, Spillantini MG, Jakes R, Rutherford D, Crowther RA., Multiple isoforms of human microtubule-associated protein tau, sequences and localization in neurofibrillary tangles of Alzheimer's disease, *Neuron.*, 3:519–26 (1989).

Goedert M, Jakes R., Expression of separate isoforms of human tau protein, correlation with the tau pattern in brain and effects on tubulin polymerization, *EMBO J.*, 9:4225–30 (1990).

Goedert M, Jakes R, Crowther RA, Cohen P, Vanmechelen E, Vandermeeren M, Cras P., Epitope mapping of monoclonal antibodies to the paired helical filaments of Alzheimer's disease, identification of phosphorylation sites in tau protein, *Biochem J.*, 301:871–7 (1994).

Goedert M, Spillantini M G, Crowther R A, Chen S G, Parchi P, Tabaton M, Lanska D J, Markesbery W R, Wilhelmsen K C, Dickson D W, Petersen R B, Gambetti P., Tau gene mutation in familial progressive subcortical gliosis, *Nat. Med.*, 5:454–7 (1999).

Gotz j, Probst A, Spillantini MG, Schafer T, Jakes R, Burki K, Goedert M., Somatodendritic localization and hyperphosphorylation of tau protein in transgenic mice expressing the longest human brain tau isoform, *EMBO J.* 14:1304–13 (1995).

Grover A, Houlden H, Baker M, Adamson J, Lewis J, Prihar G, Pickering-Brown S, Duff K, Hutton M., 5' splice site mutations in tau associated with the inherited dementia FTDP-17 affect a stem-loop structure that regulates alternative splicing of exon 10, *J. Biol. Chem.*, 274:15134–43 (1999).

Hardy J, Duff K, Hardy KG, Perez-Tur J, Hutton M., Genetic dissection of Alzheimer's disease and related dementias, amyloid and its relationship to tau, *Nat. Neurosci.*, 1:355–8 (1998).

Hasegawa M, Smith M J, Goedert M., Tau proteins with FTDP-17 mutations have a reduced ability to promote microtubule assembly, *FEBS Lett.*, 437:207–10 (1998).

Hong M, Zhukareva V, Vogelsberg-Ragaglia V, Wszolek Z, Reed L, Miller B I, Geschwind D H, Bird T D, McKeel D, Goate A, Morris J C, Wilhelmsen K C, Schellenberg G D, Trojanowski J Q, Lee V M., Mutation-specific functional impairments in distinct tau isoforms of hereditary FTDP-17, *Science.*, 282:1914–7 (1998).

Hutton, M., Lendon, C. L., Rizzu, P. and the FTDP-17 collaborative group., Association of missense and splice site mutation in tau with the inherited dementia FTDP-17, *Nature.*, 393,702–705 (1998).

Ikonomovic, M. D., Mizukami, K., Davies, P. Sheffield, R., Armstrong, D. M., The loss of GluR2(3) immunoreactivity precedes neurofibrillary tangles formation in the entorhinal cortex and hippocampus of Alzheimer's brains, *J. Neuropath. Exp. Neurol.*, 56, 1018–1027 (1997).

Iqbal K, Grundke-Iqbal I., Molecular mechanism of Alzheimer's neurofibrillary degeneration and therapeutic intervention, *Ann NY Acad. Sci.*, 777:132–8 (1996).

Jicha, G. A., Bowser, R., Kazam, I. G. and Davies, P., Alz-50 and MC-1, a new monoclonal antibody raised to paired helical filaments, recognize conformational epitopes on recombinant tau, *J. Neuroscience Research.*, 48:128–132 (1997).

Jicha, G. A., Lane, E., Vincent, I. J., Otvos, L., Hoffmann, R. Davies, P. A., Conformation and phosphorylation dependent antibody recognizing the paired helical filaments of Alzheimer's Disease, *J. Neurochem.*, 69:2087–2095 (1997).

Jicha GA, Berenfeld B, Davies P., Sequence requirements for formation of conformational variants of tau similar to those found in Alzheimer's disease, *J. Neurosci Res.*, 55:713–23 (1999).

Kampers T, Pangalos M, Geerts H, Wiech H, Mandelkow E., Assembly of paired helical filaments from mouse tau, implications for the neurofibrillary pathology in transgenic mouse models for Alzheimer's disease, *FFBS Lett.*, 451: 39–44 (1999).

Kosik K S, Crandall J E, Mufson E J, Neve R L., Tau in situ hybridization in normal and Alzheimer brain, localization in the somatodendritic compartment, *Ann Neurol.*, 26:352–61 (1989).

Lewis, J., McGowan, E., Rockwood, J., Melrose, H., Nacharaju, P., Gwinn-Hardy, K., Murphy, M., Baker, M., Hardy, J., Yu, X., Duff, K., Corral, A., Lin, W-L, Yen, S-H, Dickson, D., Davies, P., Hutton, M., Neurofibrillary tangles, amyotrophy, and progressive motor disturbance in tau mutant (P301L) transgenic mice, *Nat Genet.*, 4:402–5 (2000).

Lynch T, Sano M, Marder K S, Bell K L, Foster N L, Defendini R F, Sima A A, Keohane C, Nygaard T G, Fahn S, et al., Clinical characteristics of a family with chromosome 17-linked disinhibition-dementia-parkinsonism-amyotrophy complex, *Neurology,* 44:1878–84 (1994).

Poorkaj P, Bird T D, Wijsman E, Nemens E, Garruto R M, Anderson L, Andreadis A, Wiederholt W C, Raskind M, Schellenberg G D., Tau is a candidate gene for chromosome 17 frontotemporal dementia, *Ann Neurol.*, 43:815–25 (1998).

Reed L A, Schmidt M L, Wszolek Z K, Balin B J, Soontornniyomkij V, Lee V M, Trojanowski J Q, Schelper R L., The neuropathology of a chromosome 17-linked autosomal dominant parkinsonism and dementia ("pallido-ponto-nigral degeneration"), *J. Neuropathol Exp. Neurol.*, 57:588–601 (1998).

Reed L A, Grabowski T J, Schmidt M L, Morris J C, Goate A, Solodkin A, Van Hoesen G W, Schelper R L, Talbot C J, Wragg M A, Trojanowski J Q., Autosomal dominant dementia with widespread neurofibrillary tangles, *Ann Neurol.*, 42:564–72 (1997).

Spillantini M G, Crowther R A, Goedert M (1996) Comparison of the neurofibrillary pathology in Alzheimer's disease and familial presenile dementia with tangles, Acta Neuropathol (Berl); 92:42–8.

Spillantini M G, Goedert M, Crowther R A, Murrell J R, Farlow M R, Ghetti B., Familial multiple system tauopathy with presenile dementia, a disease with abundant neuronal and glial tau filaments, *Proc. Natl. Acad. Sci. USA.*, 94:4113–8 (1997).

Spillantini M G, Goedert M., Tau protein pathology in neurodegenerative diseases, *Trends Neurosci,* 21:428–33 (1998).

Spillantini M G, Murrell J R, Goedert M, Farlow M R, Klug A, Ghetti B., Mutation in the tau gene in familial multiple system tauopathy with presenile dementia, *Proc. Natl. Acad. Sci. USA,* 95:7737–41 (1998).

Zhou L, Miller B L, McDaniel C H, Kelly L, Kim O J, Miller C A Frontotemporal dementia, neuropil spheroids and presynaptic terminal degeneration, *Ann Neurol,* 44:99–109 (1998).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A transgenic mouse, the genome of the cells of which stably comprise a DNA molecule which comprises a human genomic DNA sequence comprising a human tau promoter and which DNA sequence encodes human tau, wherein the DNA sequence is expressed in the transgenic mouse so as to result in the transgenic mouse expressing six isoforms of human tau, wherein the transgenic mouse does not express endogenous murine tau, wherein the DNA sequence comprises one SrfI restriction site in the human tau coding region, and wherein the transgenic mouse accumulates filamentous tau in dendrites of hippocampal neurons.

2. The transgenic mouse of claim 1 which accumulates abnormal tau in the cell bodies and dendrites of neurons in the hippocampus, neocortex or brainstem.

3. The transgenic mouse of claim 1 wherein at least one human tau isoform has an abnormal confirmation.

4. Progeny of the transgenic mouse of claim 1.

5. A method for expression of human tau in a mouse, comprising crossing a transgenic mouse, the genome of the cells of which stably comprise a DNA molecule which comprises a human genomic DNA sequence comprising a human tau promoter and which DNA sequence encodes human tau, wherein the DNA sequence is expressed in the transgenic mouse so as to result in the transgenic mouse expressing six isoforms of human tau, wherein the DNA sequence comprises one SrfI restriction site in the human tau coding region, with a mouse that does not express endogenous murine tau, to yield the transgenic mouse of claim 1.

6. The method of claim 5 wherein the human tau isoform has an abnormal conformation.

* * * * *